(12) United States Patent
Ugolin et al.

(10) Patent No.: US 8,241,893 B2
(45) Date of Patent: Aug. 14, 2012

(54) METHOD AND DEVICE FOR SEPARATING MOLECULAR TARGETS IN A COMPLEX MIXTURE

(75) Inventors: Nicolas Ugolin, Paris (FR); Sylvie Chevillard, Le Kremlin Bicetre (FR); Alexadre Coutant, Issy-les-Moulinaux (FR); Jerome LeBeau, Paris (FR)

(73) Assignee: Commissariat a l 'Energie Atomique, Paris (FR)

( * ) Notice: Subject to any disclaimer, the term of this patent is extended or adjusted under 35 U.S.C. 154(b) by 536 days.

(21) Appl. No.: 11/892,672

(22) Filed: Aug. 24, 2007

(65) Prior Publication Data
US 2008/0182758 A1    Jul. 31, 2008

Related U.S. Application Data

(63) Continuation of application No. PCT/FR2006/000428, filed on Feb. 24, 2006.

(30) Foreign Application Priority Data

Feb. 25, 2005  (FR) ..................................... 05 01962
Feb. 28, 2005  (FR) ..................................... 05 02027

(51) Int. Cl.
 *C12M 1/36* (2006.01)
 *G01N 15/06* (2006.01)
 *C07H 21/04* (2006.01)
(52) U.S. Cl. ..................... 435/287.2; 435/6.1; 422/68.1; 422/82.01; 536/23.1
(58) Field of Classification Search ........................ None
See application file for complete search history.

(56) References Cited

U.S. PATENT DOCUMENTS 5,665,539 A    9/1997  Sano et al.
5,846,708 A    12/1998 Hollis et al.
(Continued)

FOREIGN PATENT DOCUMENTS

WO      WO 97/39145    * 10/1997

OTHER PUBLICATIONS

Sakata et al. "Immobilization of oligonucleotide probes on Si3N4 surface and its application to genetic field effect transistor" Materials Science and Engineering C, 2004, 24: 827-832.*
Cuzin, Tranfus Clin Biol. vol. 8, pp. 291-296, (2001).
Bertucci et al., Human Molecular Genetics, vol. 8, No. 9, pp. 1715-1722, (1999).

(Continued)

*Primary Examiner* — Betty Forman
(74) *Attorney, Agent, or Firm* — Birch, Stewart, Kolasch & Birch, LLP.

(57) ABSTRACT

The invention relates to a method of analysing molecular targets contained in a complex mixture, comprising the following steps consisting in: a) bringing the mixture of molecular targets to be analysed into contact with an array of different types of primary probes, whereby each type of primary probe forming the array can bind specifically to a type of target selected from among the molecular targets, under conditions that enable specific binding between the molecular targets and the primary probes; b) optionally eliminating the primary probes that are not bound specifically to a molecular target; c) separating the molecular targets and the primary probes which are bound specifically in a probe/target complex, such as to recover the array of primary probes representing a fingerprint of the molecular targets to be analysed; and d) quantitatively analysing the primary probes eluted in step c.

47 Claims, 22 Drawing Sheets
(6 of 22 Drawing Sheet(s) Filed in Color)

U.S. PATENT DOCUMENTS

| | | | |
|---|---|---|---|
| 6,818,109 B2 * | 11/2004 | Hashimoto et al. | 204/403.04 |
| 7,443,507 B2 * | 10/2008 | Ran et al. | 356/445 |
| 2003/0036064 A1 | 2/2003 | Stuelpnagel et al. | |
| 2003/0148335 A1 | 8/2003 | Shen et al. | |
| 2005/0003360 A1 | 1/2005 | Huang | |
| 2005/0221473 A1 * | 10/2005 | Dubin et al. | 435/287.2 |
| 2006/0239864 A1 * | 10/2006 | Ugolin et al. | 422/101 |

OTHER PUBLICATIONS

Martinez et al., Nucleic Acids Research, vol. 31, No. 4, e18, pp. 1-8, (2003).

Hoen et al., Nucleic Acids Research, vol. 31, No. 5, e20, pp. 1-8, (2003).

* cited by examiner

METHOD AND DEVICE FOR SEPARATING MOLECULAR TARGETS IN A COMPLEX MIXTURE

The invention relates to a method and a device for analysing molecular targets in a complex mixture. Specifically, the invention allows the separation and quantitative analysis of molecular targets in a complex mixture.

A particular object of the invention is a means for remedying, at least in part, the difficulties encountered hitherto for separating and analysing molecular targets using organised matrices of biopolymer probes, known in prior art.

BACKGROUND OF THE INVENTION

Organised matrices of biopolymer probes (DNA chips, protein chips, etc.) make it possible to separate qualitatively and quantitatively biopolymers (molecular targets) present in a mixture, and this is theoretically possible whatever their number, sequence and complexity. However, the nucleic acid networks do not allow absolute and accurate counting of the number of target molecules hybridised to the probes. With currently available technology, detecting biopolymers on microarrays is indirect, necessitating a labelling step (using fluorescence, radioactivity . . . ). By way of example, the method using "fluorescent labels" measures the intensity of fluorescence of the fluorescent labels bound to the molecules to be analysed.

When a molecule is hybridised, it produces an increase in fluorescence which is proportional to the number of probe-target complexes formed on a microarray. However, the indirect measurements using labels are only relatively reliable, particularly when the molecular targets form a small quantity of biological material to be analysed or these measurements have drawbacks for use in routine analyses.

Although the yields from incorporating radioactively labelled residues and cold residues into biopolymers are almost identical, the same cannot be said for fluorescent labels (Martinez et al. —Nucl. Acids. Res. 2003 31: p. 18; Hoen et al. —Nucleic Acids Res. 2003 Mar. 1; 31(5); p. 20). These labelling problems are encountered particularly for the synthesis of cDNA molecules incorporating the fluorescent labels CY3 and CY5. The steric hindrance resulting from this latter type of labelling can also greatly modify the kinetics and stoichiometric equilibria of the reactions (hybridisation, antibody-antigen reaction, target-ligand reaction in general . . . ).

These problems of steric hindrance are eliminated by using radioactive isotopes; however, using radioactive isotopes necessitates handling radioactive waste as well as the issues involved with the materials used and with the safety of personnel. Also, the technologies for detecting radioactively labelled molecules, that is, mainly "Phosphoimager" type for radioactivity (Bertucci F et al. —Hum Mol Genet. 1999 September; 8(9): 1715-22. Erratum in: Hum Mol Genet 1999 October; 8(11); p. 2129), and the different types of scanner for detecting fluorescence display a certain number of limits regarding the quantity of biological material to be hybridised on a chip in order to reach the detection and reproducibility thresholds of the measurements carried out. In fact, it is not possible to detect molecules present as only a few copies per cell in samples with a small number of cells (~1 000 cells), which is a frequent situation for clinical samples.

In order to overcome the difficulties related to the need to use direct labelling of biopolymer probes, as mentioned above, other methods of detecting the probe-target complexes formed have been developed to detect these probes indirectly.

Thus, using the electrical conductance properties of biopolymers has been suggested. This is possible because a molecule of single stranded DNA of a sequence does not have the same impedance as the corresponding double stranded molecule. This property is used on DNA chips to evaluate the proportion of hybridisation, and thus the number of probe-target complexes formed on a microarray. In general, variations in impedance can be used to study the intermolecular interactions, such as the binding of a ligand on its receptor, but also the interactions between the molecules of DNA or proteins and a drug, an ion . . . . However, for microarrays, this detection method is limited:

1) By the difficulty in making high density chips of over 2000 spots. Because of the size of the electrodes and the geometry of the connections used to make impedance chips, the hybridisation surface becomes very large as soon as the number of spots exceeds 800. But a large hybridisation surface needs a large hybridisation volume, hence the need for a large quantity of biological material in order to reach the minimum level for detection. This is incompatible with the experiments where little material is available, for example for diagnoses.

2) By conformation changes in the molecules studied (probe and/or target) which cause measurement artefacts that make the variations in impedance measured un-interpretable. For example, distortions in the DNA because of sequence or intra-molecular hybridisations cause variations in impedance of the same order of magnitude as for inter-molecular hybridisation.

3) By variations in impedance due to the size of the molecules to be analysed. For example, nucleic acid molecules, representing a transcriptome, have different sizes, because of:
   The heterogeneous way the transcription proceeds from one gene to another,
   The different length of genes,
   The different splicing undergone by transcripts of the same gene.

The electrical signal measured at a spot on a chip comes therefore from the hybridisation of a heterogeneous mixture of transcript sizes for one gene. This signal is not comparable either to that obtained for the same gene hybridised in a different cell extract, or to that obtained for another gene on the same chip.

In these conditions, the measurement of impedance is also made difficult because of the following constraints. Field effect transistors are used as amplifiers of current and/or voltage to measure the changes in impedance caused by hybridisation of the DNA molecule. The grafting of the probes occurs at the transistor grid. When the targets hybridise there, they alter the impedance of the grid which causes a change in the current and voltage between the source (transistor input) and the drain (output) of the transistor. No network organisation has been described for this method of detection. Using a field effect transistor as a current amplifier by placing probes at the transistor grid, limits the use of the transistor.

This is because the grid of a field effect transistor cannot be subject to an electric current. An electrical voltage only can be applied to it which will control the opening of the source/drain channel. To measure the impedance of an oligonucleotide directly and effectively, it is necessary to subject it directly to voltages and/or alternating currents of different frequencies. Furthermore, the weakness of a field effect transistor grid makes it difficult to protect from static electricity produced during positioning of the probes.

The presence of probes on the grid also precludes use of the transistors as switches in a multiplexer, to control voltage and current flow at each spot. Also in this configuration, it is not possible to use the sources and drains of the transistors as an electrophoresis electrode to control the movement of target molecules over the hybridisation substrate, in order to move and concentrate the targets at each spot.

In the current state of the art, the measurement of electrical impedance of nucleic acids does not allow the quantification or analysis of the concentrations or the proportions of a heterogeneous population of molecules constituting a complex mixture of nucleic acids.

Another detection method used in this field is mass spectrometry. It is known how to determine the mass of macromolecules such as DNA, RNA or proteins by mass spectrometry. If analysis by this method is accompanied by gentle molecular breakdown, it is also possible to determine their sequence. However, in the field of complex mixtures, in particular a mixture comprising more than 100 target molecules to analyse, of which it is not known whether they are distinguishable by size or mass, it becomes difficult, or even impossible to analyse the targets.

Another possible detection method uses plasmonic surface resonance (PSR) which allows determination of the density of material accumulated a small distance (less than 200 nm) from the surface of an ultra thin (x nm) sheet of a metal with a free electron such as gold or platinum. The reflection on one of the faces of the metal sheet changes in proportion to the density and quantity of material lying close to the other face.

The plasmonic surface resonance (PSR) measures changes in mass. At hybridisation, a molecule acquires a certain mass which is proportional to the number of probe-target complexes formed on a microarray.

This method is therefore susceptible to problems similar to those described above for quantitative analysis of molecular targets contained in a complex mixture.

Use of these methods of separation and/or analysis of molecular targets is limited by the complexity of the mixtures to be analysed in which the molecules to be studied are of different shapes, sequences and sizes, or by the quantity of material available, hindering detection of targets collected using probes.

OBJECTS AND SUMMARY OF THE INVENTION

The object of the present invention is to offer an alternative to known methods for quantitative analysis of molecular targets contained in a complex mixture, which overcomes the limitations due to the heterogeneity or the complexity of the said molecular target population (in particular when it concerns a transcriptome or a proteome) and as a result makes it possible to use different techniques for detection of separated molecular targets, to achieve a reliable and reproducible quantitative measure of said molecular targets separated from the mixture.

The present invention also provides the means compatible with the analysis of molecular targets in a biological sample, when the quantity of biological material containing the targets is limited, in accordance with the quantities generally available to make a clinical diagnosis.

To do this, the inventors have defined the resources, comprising the probes (comprising a polynucleotide portion, including in the form of oligonucleotides) defined to constitute that which will be designated in the following as "an array of primary probes". When it is placed in contact with the complex mixture of targets to be analysed, specifically in solution, the array of primary probes is able to produce a molecular fingerprint of said targets, reproducible from one analysis to another and able to be quantitatively detected, including by the means of detection known at this moment.

The fingerprint of the molecular targets to be detected is thus substituted for the targets, in the detection phase.

The term "fingerprint" as used herein signifies that the group of primary probes of the array of probes considered, which have actually formed a specific bond with the molecular targets, symbolises significantly, quantitatively and qualitatively the molecular targets contained in the analysed mixture, without each probe necessarily being identical, for example, in terms of composition, size and shape to the target to which it has bound. The method according to the invention frees one from having to identify or recognise specific sequences of nucleic acid targets or the specific composition of polypeptide targets.

The probes in the array of primary probes are characterised in that they comprise or, according to the embodiments of the invention consist of a molecule of single stranded nucleic acid (polynucleotide), or a modified single stranded polynucleotide, for example of which one of the ends hybridises with a complementary sequence shorter than the single strand or for example in that they are PNA (Peptide Nucleic Acid). The term polynucleotide therefore covers modified forms that can however also be explicitly cited in the following when they are used specifically. The PNA mentioned above improves probe resolution in mass spectrometry. It is therefore particularly important when carrying out the embodiments of the invention which use this method of detection.

The array of primary probes is formed by the association, to be used as a mixture, particularly in solution, of several types of probes, each type of probe being distinguishable from each other type of probe in the array of probes and being individually detectable (in particular, quantifiable). The probes of the array of primary probes outlined in the context of the invention are able, and designed to recognise and bind specifically to, a type of target when it is present in the complex mixture analysed. In summary, for a type of primary probe there is a corresponding unique type of target in a complex mixture. It is the targets which, in the mixture, bind specifically to the primary probes which are detectable and quantifiable. The group of probes forming probe-target complexes makes the fingerprint of the targets analysed.

Further, the different types of primary probes are characterised by the absence of labelling of the polynucleotide portion by labels of the colour or luminescent, affinity, enzymatic, magnetic, thermal or electrical type, (in particular by the absence of fluorescent or radioactive label) which would be designed to allow their detection and/or quantification. Under these conditions, the individual detection of probes in the primary probe array having formed a specific probe-target complex uses at least one of the following three characteristics of the polynucleotide portion of the probe, characteristics which are called "indirect labels" giving a probe a unique self-determining characteristic and not altering its affinity for its target: (i) the composition and sequence of the nucleotides included in the polynucleotide of the probe; (ii) the size (or length) of the polynucleotide of the probe; (iii) the mass of the polynucleotide of the probe.

In a particular embodiment, as will be seen in the following description of the primary probes, the composition of the primary probes is such that either the size of their nucleic acid sequences is known and homogeneous or even identical, or, when the probes comprise a polynucleotide portion linked to a polypeptide portion, their polynucleotide sequences are of identical size.

In another embodiment of the invention, the primary probes are composed of polynucleotides of which the size and/or mass is different from the other polynucleotides in the array of primary probes.

In one variant, when the probes have both a polypeptide and polynucleotide portion, their polynucleotide portion can be measured for example by its mass and/or its size, each polynucleotide portion having a mass and/or size different from the other polynucleotides in the array of primary probes.

The object of the invention is therefore, an array of primary probes suitable for analysing molecular targets in a complex mixture, comprising a population of primary probes of different types, in solution, in which:
  each type of primary probe is different from the other types of primary probes in the array of probes,
  every primary probe is capable of binding, by a specific bond, to a unique type of molecular target to be analysed, when said primary probes and said molecular targets are brought into contact,
  each type of primary probe is a polynucleotide or alternatively comprises a polynucleotide joined to a polypeptide portion, and is capable of binding specifically to a unique type of molecular target in a complex mixture, each polynucleotide being different from the polynucleotides of all the other primary probes in the array of probes, either in the sequence of nucleotides of which it is composed, or in its size, or in its mass.

These properties of the probes in the array of primary probes are illustrated and completed by the characteristics documented below in the statement of the different embodiments, characteristics that define particular probes.

In one particular embodiment of the invention, in the array of probes thus defined, each polynucleotide is identified relative to the others and, in particular, is known independently by its sequence or by a portion of its sequence when said polynucleotide is intended to be used in a specific hybridisation reaction either to make a secondary polynucleotide-probe complex (described below) or to form a probe-target complex. In this case, the specific order of the nucleotides composing the polynucleotide, is determined or can be determined and known as being different from that of sequences of the polynucleotides of other types of probes.

If the detection of the primary probe polynucleotide does not cause a specific hybridisation reaction with a complementary nucleic acid sequence, then the polynucleotide of each type of primary probe need only differ from the polynucleotides of the other primary probes in its size and/or its mass. This difference in size (total number of nucleotides in the empirical formula, giving the length of the probe polynucleotide), and/or in its mass (calculated from the empirical formula of the sequence), taking account of the number of each of the nucleotides of which it is composed and the mass of each within the array of probes, and taking into consideration the possible modifications to said sequence to alter the mass relative to the mass of the sequence initially identified to incorporate an appropriate polynucleotide in a probe-target complex.

These three criteria (sequence, size and mass) allow production of a considerable number of different primary probes. In considering the empirical formula: $(A_n, C_m, T_i, G_j)$ in which A is Adenosine, C is Cytosine, T is Thymine, G is Guanine, and n, m, i, j are their respective numbers in the formula (the size of the nucleic acid polymer is equal to $(n+m+i+j)$, it is possible to generate a number equal to $(n+m+i+j)!/(n!.m!.i!.j!)$ different probes without including possible modifications to alter the mass (x! denotes x factorial).

In the case where the mass of the polynucleotide for each type of primary probe is known and different for each type of probe, the analysis of primary probes, that is to say the identification of primary probes which are bound specifically to molecular targets, is done after a step to determine the masses of their polynucleotides. This measurement can be done by mass spectrometry.

The mass of the polynucleotide of one type of primary probe must be easily distinguishable from the masses of the polynucleotides of all the other types of primary probes.

When the masses of two polynucleotides corresponding to two types of primary probe are close, that is to say liable to be confused in one detection method, for example in mass spectrometry, the mass of at least one of them can be altered for example by substitution of certain of its atoms by heavier atoms or by methylation or ethylation of some of its bases (A, T, C, G) such as cytosine, in order to make them more easily distinguishable.

In the case of a array of primary probes containing several hundred or even several thousand or several tens or hundreds of thousands of different types of primary probes, it is advantageous to modify in this way the masses of their polynucleotides in a logical manner in order to be able to identify more easily the different types of polynucleotides at the primary probe analysis stage.

The analysis step for primary probes bound specifically to molecular targets in a test sample and of which the polynucleotides have different masses can consist in:
  Preparing a standard mixture of probes containing the same array of probes as the primary probe array intended for the sample analysis but altering the mass of each probe by an amount for example equivalent to one unit of resolution on the mass spectrometer,
  analysing by mass spectrometry the polynucleotides (present in known amounts) of the primary probes which are bound specifically to molecular targets in such a way as to obtain a mass spectrogram, in the presence of a known quantity of probes of the standard mixture used at several dilutions, and if necessary verifying that the mass of each standard probe modified by the aforementioned unit of resolution does not overlap the mass of any probe in the array of probes tested, this step constituting the preparation of a reference spectrogram
  adding to the fingerprint obtained for the sample analysed, using the probes of the array of primary probes, a known quantity of the standard mixture and obtaining a mass spectrogram for this mixture;
  comparing the mass spectrogram in the above step with the reference mass spectrogram so as to quantify the target molecules through the quantification of the probes in the array of primary probes forming the aforesaid fingerprint.

In the case where the mass of the polynucleotide for each type of primary probe is known and different for each type of probe, the analysis of primary probes, that is to say the identification of primary probes which are bound specifically to molecular targets, is done after a step to determine the masses of their polynucleotides. The determination can be performed with an electrophoretic separation system, by filtration or by chromatography, in the gaseous or liquid phase, coupled to a UV detection system or by LIBS (Laser Induced Breakdown Spectroscopy).

As described previously, it can be advantageous to modify the polynucleotides chosen for use in constructing primary probes to give them different physical-chemical properties (by a given number of methylations, ethylations, etc.) so as to be more easily identified at the primary probe analysis stage, in particular when different polynucleotides used in probes have the same mass.

In this case, and when the targets are nucleic acids, the preparation of a array of primary probes of which the polynucleotide portion is comprised in this way can be carried out, in particular when there is a need to obtain a large number of probes, following the steps shown in FIG. 22 and described below, these steps being performed with the aid of a computer programme when the number of probes requires this.

Step 110: defining a size interval for the primary probes, for example composed of polynucleotides comprising from 20 to 150, for example 20 to 100 nucleotides and defining the conditions for hybridisation of probes and targets and in particular the melting temperature Tm (the temperature at which 50% of a given probe hybridises to its complementary sequence), comprised for example between 50 and 75° C. for the group of probes.

Steps $120_1$, $120_2$ and $120_3$: determining the number S of polynucleotide molecular targets of different sequences, if necessary after discarding the regions of the target not wanted for preparing probes. This number can be greater than or equal to 10, 50, 100, 500, 1000, 10 000, 20 000 or more. Each of the target sequences has a number i, this number being comprised between 1 and S.

Steps $130_1$ and $130_2$: the identification, for each target sequence i potentially present in a sample, of a collection of $N_i$ possible probes perfectly hybridisable by the target under consideration and of which the size is comprised in the chosen size interval and the Tm is comprised within the chosen values.

Steps $140_1$ and $140_2$: the selection within the aforementioned collection of $N_i$ sequences, of a population of $n_i$ polynucleotide sequences able to bind by hybridisation to the molecular target comprised by the considered sequence i and of which the bond thus formed is specific, excluding from then on a hybridisation with other possible target sequences of the mixture. For this, each probe in the collection of $N_i$ probes is compared with all the i sequences likely to be in the sample, for example with the help of databases such as EMBL, Genebank . . . . Each population of $n_i$ probes is specific for a unique molecular target sequence i. The sequences of primary probes which show a similarity over a certain threshold with other sequences in the collection of $N_i$ probes, for example a threshold of 15 consecutive identical bases, can be eliminated.

Steps $150_1$ and $150_2$: within this population of $n_i$ putative polynucleotides for making up the probes, assigning to each polynucleotide, of a mass different from the mass of the other polynucleotides in the population, if necessary by modifying the nucleotides contained therein, for example by methylation or ethylation of one or several cytosine residues, to obtain a collection of polynucleotides where each sequence has a known and different mass. For each sequence modification the comparison is repeated recursively. The population of $n_i$ polynucleotides is preferably ranked in order of increasing mass then in order of increasing number of methylations or other modifications.

Steps $160_1$ and $160_2$: For i=1, that is to say for the sequence of the first molecular target considered, there exist Zi combinations of 1 primary probe ($Z_i$ being equal to $n_i$).

Steps $170_1$, $170_2$ and $170_3$: For the target i, i different from 1 and for example equal to 2, the aforementioned steps are repeated for the identification of a population of $n_i$ primary probes all having a different mass and being capable of hybridising to the target sequence i. A collection is described of $Z_i$ combinations of primary probes, each one of these combinations comprising a unique primary probe for each population of $n_i$ probes studied, or to put it another way, each one of the i primary probes is derived from one and only one of the i sequences considered, the group of primary probes for each of the $Z_i$ combinations being such that all the polynucleotides have a different mass. For this, each primary probe of the population of $n_i$ probes is compared with primary probes of the combinations detailed above, that is to say of each combination $m_{(i-1)}$, $m_{(i-1)}$ ranging from 1 to $Z_{i-1}$. When the masses of the primary probes are too close to each other, the primary probe containing the fewest modifications, for example the fewest methyl or ethyl groups can be methylated, for example on the first 5' non-methylated or non-ethylated cytosine. For each sequence modification the comparison is repeated recursively.

Step 180: The $Z_i$ combinations of i primary probes are ranked in ascending order, by the sum of the masses of the primary probes which comprise the combination, then ranked in ascending order by the number of modified residues for example of methyl or ethyl groups on the primary probes in the combination, so that the primary probes having the same number of modifications within a combination are ranked by ascending order of their mass. Only one portion of the combination can be considered, for example the first Ls, to speed up the algorithm in the following step.

Step $160_2$: Identification of a collection of $Z_i$ combinations of i primary probes across the i sequences studied.

The aforementioned steps are repeated for every i, i ranging from 3 to S. When i=S and a collection of $Z_s$ combinations of S primary probes has been identified for the S target sequences, one of the combinations can be chosen which will constitute the primary probe array. Preferably this combination is that which is either easiest to accomplish in terms of time and cost, or that which is first in the ranking of the $Z_s$ combinations constructed in step 180.

The primary probes in the probe array thus defined are synthesised by any known method for the preparation of polynucleotides. More generally, the primary probe array is prepared by the method comprising the steps consisting in:

defining a size interval for the primary probes and defining the conditions for hybridisation of probes to targets and in particular the melting temperature Tm for the group of probes, determining the number i of polynucleotide molecular targets of different sequences in a complex mixture identifying, for each target sequence i potentially present in the sample, of a collection of $N_i$ possible probes perfectly hybridisable by the target under consideration and of which the size is comprised within the chosen size interval and the Tm is comprised within the chosen values, selecting within the aforementioned collection of $N_i$ probes, a population of $n_i$ polynucleotide sequences able to bind by hybridisation to the molecular target constituted by the considered sequence i and of which the bond thus formed is specific, excluding from then on a hybridisation with the other possible target sequences of the mixture, within this population of putative probes for making up the probes, assigning to each polynucleotide, a mass different from the mass of the other polynucleotides in the population, if necessary modifying the nucleotides contained therein, for example by methylation or ethylation of one or several cytosine residues, to obtain a collection of polynucleotides all having a mass known and different for each sequence, the comparison being repeated recursively for each sequence modification, identifying a collection of $Z_i$ combinations of i primary probes for each sequence i, each one of these combinations comprising a unique primary probe for each population of $n_i$ probes studied; each one of the primary probes of the population of $n_i$ probes being compared with primary probes in the combinations created above, and when the masses of the primary probes are too close to each other, modifying their sequence, the comparison being repeated recursively for each sequence modification, ranking the $Z_i$ combinations of i primary probes in ascending order, by the sum of the masses of the i primary probes which comprise the combination and in ascending order by the number of modified groups identifying a collection of $Z_i$ combinations of i primary probes across the i sequences studied, synthesising the primary probes in the probe array thus defined.

When the sample targets are not nucleic acids, the method for preparing the polynucleotides contained in the primary probes is varied with respect to the description above, in as much as it is not necessary to consider a specific hybridisation reaction between the probes and targets.

When the mass is not a distinguishing criterion for detecting the primary probe polynucleotides, they can be distinguished by size and/or sequence. Whatever the primary probe polynucleotide size and mass characteristics, the polynucleotide sequence of each type of primary probe in the case where the targets are nucleic acids must be different from all the other sequences of the other types of primary probes, in order to allow specific and exclusive binding to a target. The specificity thus defined of the polynucleotide sequence can according to one embodiment of the invention constitute the means of detecting the primary probe and thus of the target.

When the detection of primary probes in target-probe complexes calls upon detection of the polynucleotide sequences, use can be made of an array of secondary probes as described below. FIG. 22 shows an example of the strategy to obtain a mixture of 1000 primary probes differentiated by their mass. Choice of the mass of each primary probe is a function of sequence, of size and/or modification of the nucleic acid bases, for example by adding methyl groups to the cytosines. The primary probe array can be intended to be analysed in a MALDI-TOFF mass spectrometer with a resolution of 13 daltons. Alteration of the mass of a primary probe can be achieved by substitution of several atoms by heavy isotopes.

A similar approach can be envisaged to make a primary probe array with specific chromatographic criteria for each primary probe, taking into account the size of the primary probes, and the positions of methylations and substitutions performed. For use in the context of the invention, the primary probe array comprises an excess of each type of primary probe with respect to the quantity of target it can recognise in the complex mixture. Further, the primary probe array is used in the form of a stoichiometric mixture of primary probes.

To maintain the stoichiometry of the probe mixture, the probes are prepared such that their polynucleotide portions cannot hybridise with themselves, or at least cannot form stable probe-probe hybrids.

Thus the inventors have shown that probes that are indirectly labelled (with a molecule that is itself detectable) can be used in a mixture, to obtain a characteristic and reproducible fingerprint of heterogeneous molecular targets in a complex mixture for analysis, said fingerprint being made up of probes having formed probe-target complexes in solution or of the polynucleotide portion of the latter, and able to be quantitatively measured, to determine the quantity of targets contained in the mixture.

Said probes (or their polynucleotide portion) can further be individually identified and quantified after forming probe-target complexes in solution after being placed in contact with a mixture of targets. This identification consists in the identification of their polynucleotide portion by detection of an effect due to the nucleotide sequence of the polynucleotide, to its size or to its mass.

So the object of the invention is a primary probe array in a stoichiometric mixture suitable for analysis of molecular targets in a complex mixture comprising a population of primary probes of different types, in solution, in which each type of primary probe constituting the array is different from the other types of probes at the nucleotide sequence of the polynucleotide it contains and/or according to the particular embodiments of the invention differs in the mass of said polynucleotide or in its size or in the two last criteria, able to bind specifically to one type of molecular target to be analysed, when said primary probes and said molecular targets are placed in contact and caused to react in solution.

In a particular embodiment of the invention, the primary probe array consists in at least 10 primary probes, for example at least 50, particularly at least 100, preferably at least 200, advantageously at least 1000 or at least 10 000 or 20 000 probes.

The method according to the invention analyses the molecular targets by means of primary probes. As indicated above, the primary probes, without necessarily being made exclusively of nucleic acids, contain a polynucleotide portion. This polynucleotide portion must be detectable, optionally by secondary detection probes for example for polynucleotides of homogeneous or identical size, or by other means, for example by determining the differences in size or mass or other known physical-chemical properties of the polynucleotides according to their structure. The primary probes having actually bonded specifically with the molecular targets represent a sub-group of the primary probes in the array of probes used initially, that constitute a fingerprint of the molecular targets to be detected contained within the mixture.

In an embodiment of the analysis of a complex nucleic acid mixture, (unlike the molecular targets to be analysed, of which the size and/or the sequence can be indeterminate, or even unknown), the primary probes can be chosen so as to all have a homogeneous size, for example identical or, when the probes combine a polypeptide and a polynucleotide portion, the size of the latter is homogeneous, for example identical, amongst the probes. Those skilled in the art are able to determine what size variation between the probes is acceptable, particularly contingent upon the sensitivity of the electrical or optical detection method being used. By way of indication, it will be considered that the size of the probes is homogeneous when they vary in a range of ±x % with respect to a chosen size if the detection measurements are accurate to ±x %. In practice, a size variation in a range of about ±10% would be acceptable.

In addition, the sequence of each type of primary probe (or the nucleotide portion of a primary probe) is known or can be determined. In particular these sequences are linear. The variations in measurement caused by each probe can be measured contingent upon sequence.

The primary probes or their polynucleotide portion, of which the size and the sequence are known or can be measured which are bound specifically to the molecular targets in an analysed mixture are then separated from their target and recovered (eluted) for analysis, for example by means of secondary polynucleotide probes. The use of secondary probes in a hybridisation reaction with the eluted primary probes, allows identification and quantification of said primary probes and indirect identification and quantification of the molecular targets. The secondary probes in question are characterised in the same way as the primary probes made up of polynucleotides by considering that in this case their targets are the primary probes.

The detection of the pairings formed between the primary probes (or their polynucleotide portion) and the secondary probes can be carried out without the primary probes needing to be labelled, as shown below.

Said eluted primary probes can be detected by keeping them in a matrix of secondary probes of different types, each secondary probe having a sequence able to retain a unique type of primary probe by a specific bond in molecular hybridisation. The secondary probes used form an array of probes with a similar size to that of the array of primary probes in contact with a complex mixture.

The present invention therefore makes it possible, in the context of analysis of a complex nucleic acid mixture, when using an array of primary probes and an array of secondary probes at the same time, brought in contact on a single chip, to make measurements dependent only on the abundance of each type of probe and to avoid measurement artefacts due to the presence of molecular targets with different sizes, shapes and sequences.

In the context of analysis of a complex mixture of molecular targets which are not nucleic acid molecules, for example proteins or any other sorts of molecule capable of forming a specific probe-target complex (for example sugars, lipids . . . ), the present invention proposes a primary probe array constituted such that it represents a range of probes of which the polynucleotide portions are distinguishable for each probe by a different sequence and a homogeneous, or identical size in the probe array, or alternatively each polynucleotide portion is distinguishable from the others by having a different mass or a different size. The polynucleotide portions of the probes are separated from the probe-target complexes formed in the mixture in solution, to be analysed for example by hybridisation to secondary probes, by mass spectrometry, chromatography, filtration or electrophoresis.

That which has been described above concerning the nucleotide sequences of the primary probe polynucleotides applies expressly to polynucleotide portions of primary probes when they also comprise a polypeptide portion, except in the case of the steps involving the target nucleic acids Within the scope of the above definitions, the present invention therefore relates to a method of analysing molecular targets, contained in a complex mixture comprising:

a. placing in contact the complex mixture liable to contain the molecular targets for analysis with an array of different types of primary probes, each type of primary probe composing the array being capable of binding by a specific bond to a type of target among the molecular targets, in conditions allowing the specific binding of said molecular targets and said primary probes, b. optionally removing the primary probes not specifically bound to a molecular target, c. separating the molecular target-primary probe complexes formed by specific binding, so as to recover the primary probes representing a fingerprint of the molecular targets contained in the mixture and recognised by the primary probes, d. analysing the primary probes eluted in step c.

Advantageously, the method of the invention allows quantitative analysis of the primary probes eluted in step c.

Quantifying these primary probes (or their polynucleotide portions) separated from the molecular targets allows quantitative analysis of the molecular targets the quantity of which is proportional to that of the separated primary probes.

The expression "complex mixture" as used in the context of the invention, should be understood to mean a solution comprising a large number of molecules with different structures (notably sequences), in particular a mixture of more than 10, particularly more than 50 more than 100 or more than 1000, or more than 10 000 or 20 000 molecules having different structures. The device of the invention is intended preferably for analysing biological molecules (or bio-molecules such as nucleic acids or proteins), particularly those contained in a biological sample. In particular, the complex mixture is a transcriptome or representation of a transcriptome (in the form of cDNA) or is a proteome.

The invention also allows analysis of a complex mixture comprising both nucleic acid targets and polypeptide targets. In this particular case, the two populations of targets must be able to be distinguished from each other by the analysis. This distinction can be made by the choice of a specific primary probe array for each population.

More particularly, the sample providing the complex mixture can be from a tissue sample or a biological fluid, such as blood, serum, plasma, cerebrospinal fluid, urine or saliva. The sample can be from an animal (in particular a mammal and preferably a human). The sample can in particular be from a healthy individual or a patient with a medical condition. The condition can be particularly a cancer, a neuro-degenerative disease, an infection and particularly a viral, bacterial or parasitic disease.

The sample can also contain a tissue extract or cell extract, from eukaryotic or prokaryotic cells, bacteria, fungi or yeasts, particularly culture cells or cells taken from the external environment. The sample can also be taken from plants. It can also be a sample of agri-food industry products, particularly from cooked food, seeds, fruits or cereals.

The expression "molecular targets" in this context is particularly understood to mean biopolymers such as DNA, RNA molecules, in particular genomic DNA or RNA, cDNA or mRNA, siRNA . . . peptides or proteins able to be recognised and specifically bound by primary probes of the invention.

To perform step a) driving the specific binding of molecular targets and primary probes, different conditions can be conceived.

In a particular embodiment of the invention this step is performed in solution.

In this embodiment, the molecular targets to be detected can be fixed to particles brought into contact with the mixture in solution. For example magnetic particles can be used. It is also possible to use magnetic beads coated with ITO or polyimide. All the targets can be adhered. Alternatively only certain types of targets may be adhered for a more specific analysis of the mixture. According to another embodiment, it is possible to use a mixture of different particles where each type of particle is directed to pick up one specified type of molecular target.

Alternatively, the molecular targets in the complex mixture to be analysed are adhered to a support. The primary probe array is then brought into contact with said support to perform step a).

Step a) is performed using a mixture with an excess of primary probe over the molecular targets. As used herein, "excess of probe" is understood to mean a quantity of probe larger than or equal to the expected quantity of molecular targets. The excess of primary probe used must allow saturation of the targets recognised and specifically bound by the probes.

To perform step a), the probes are in a stoichiometric mixture.

In a particular embodiment of the invention, the hybridisation reaction of the probes in the primary probe array is performed under thermodynamic conditions, for example in a temperature gradient and if necessary using cooling and heating plateau regions, as illustrated below in the caption for FIG. 19.

The elimination at step b), of the primary probes that have not formed probe-target complexes can be by recovering these probes to remove them from the reaction medium. This step b) can be moved and done just before bringing the primary probes separated from the probe-target complexes into contact with the means of detection. For example, the probes not having formed probe-target complexes must be separated from the other probes before bringing the latter together with the secondary probes which would be used to detect the primary probes of the molecular fingerprint.

Step c. consists in the separation of molecular target-primary probe complexes. The word "separation" used herein is understood to mean:
Either the separation of the double stranded nucleic acids (DNA-DNA, DNA-RNA . . . ) formed by hybridisation of the molecular targets and primary probes;
Or the separation of specific complexes formed between polypeptide molecular targets and primary probes (comprising for example antibodies or antibody fragments or receptors and a polynucleotide portion). Subsequently, the polynucleotide portion of the primary probes must be separated from the rest of the primary probe.
Or the separation of the polynucleotide portion of the primary probes specifically bound to the molecular targets.

"Separation" as used herein is understood to mean an operation to break the specific bond between the target and the probe or to break the bond between the polynucleotide portion of the probe and the rest of the target-probe complex. In the particular case of nucleic acid molecules, the separation equates with controlled denaturation of the hybrid formed between the two complementary strands of DNA, DNA/RNA . . . , also called dehybridisation.

In the case of protein molecular targets if the separation is of the two parts of the target-probe complex, separation is for example breaking an antigen/antibody complex (or fragment of antibody containing the antigen binding site) or ligand/receptor formed by a specific bond.

The term "specific bond" in reference to the binding of a probe to a target or a probe to a probe, means that the probe binds to a particular target or probe but does not bind in any significant way to other targets and probes and more particularly to the other targets or probes present in the complex mixture.

The expression "different types of probes" as used herein is understood to mean molecules having different polynucleotide sequences and, when the probe also contains a non-polynucleotide portion, for instance a polypeptide portion, this portion is different for each type of probe and specific for one type of target and, furthermore each polynucleotide portion is different from the polynucleotide portions of other probes and fulfils the characteristics given in the present claim. Each type of probe composing the primary probe array is specific for one unique type of target amongst those analysed.

The recovery, in step c), of the primary probes after their binding with molecular targets can be achieved by initially immobilising all the targets on particles, for example magnetic particles. In the case of targets adhered to magnetic particles a magnetic field is applied after the step binding primary probes to targets, so as to recover said primary probes.

The recovery, in step c), of the primary probes after their binding with molecular targets can be achieved by centrifugation to recover the primary probes, after having separated said probes from the "target-particle" entities.

In another particular embodiment of the invention, when the primary probes representing a fingerprint of the molecular targets contained in the analysed mixture, are recovered after having initially immobilised the molecular targets on a support then having moved the primary probes over the support under appropriate conditions to allow contact and specific binding with the molecular targets, the primary probes that have not hybridised are removed from the support then the "molecular target-primary probe" complexes are separated to recover the primary probes.

It is also possible to quantify the primary probes that were previously specifically bound to molecular targets, particularly those that were hybridised. The support used in this example is particularly a membrane, or example made of nitrocellulose, with silane or polylysine coating.

The method can be used in this way in various applications, for instance in medical diagnostics or agri-food industry quality control, or all biological analyses, particularly in the fields of ecology, archaeology or criminology.

By way of example, the method and scope of the invention allow analysis:
of nucleic acid molecules present in a mixture, for example the nucleic acid molecules (content or transcripts) by a cell or a group of cells, identical or different,
of proteins contained in a mixture, for example the proteins produced by a cell or group of cells, identical or different,
of nucleic acids and proteins contained in a mixture, produced by a cell or group of cells, identical or different.

The preferred probe-target and probe-probe pairs are particularly nucleic acids hybridising with complementary sequences such as RNA molecules, in particular messenger RNA, DNA or cDNA hybridising with specific oligonucleotide probes, antigens specifically recognising monovalent antibodies (that is to say having a single recognition site) or their monovalent functioning fragments (Fab, fragments from papain digestion or monovalent fragments having one antigen binding site, particularly a variable monovalent fragment . . . ), or all receptor-ligand or ligand-receptor pairings. In this last case, the primary probe likewise comprises a polynucleotide portion specific for a given type of molecular target and able to hybridise with the so-called secondary probes.

Those skilled in the art will be able to adapt this method to analyse all types of molecular target as long as it is possible to adhere to them a specifically recognised entity, at a single site, adhered to a polynucleotide of the molecular probe.

In a particular embodiment of the method thus defined, the molecular targets sought in the complex mixture are nucleic acids.

In a particular embodiment of the invention, the molecular targets in the mixture are nucleic acids representative of a transcriptome.

The term "representative of a transcriptome" as used herein is understood to mean nucleic acids to be analysed comprising molecular targets with sequences identical or complementary to the mRNA (or a group of RNAs) of a cell in a biological sample to be analysed. They are obtained by reverse transcription and can be cDNAs. These sequences hybridise specifically under stringent conditions, with messenger RNA (or its complement), products of transcription of genomic nucleic acid sequences of a given cell or group of cells, and are proportionally equivalent to those transcription products obtained in the specific conditions for said cell or group of cells.

A method for preparing nucleic acids representative of a transcriptome consists in using polyT primers to reverse transcribe the mRNA of a cell. In order to avoid long polyA tails, the reverse transcription of the sample messenger RNA for analysis can be done from primers, such as 5' $(T)_j X3'$ (where j is le number of T residues, j being greater than 1) for example with 5' $(T)_{19} \times 3'$ where X can be A, C or G. The reverse transcription is carried out like this starting from the first nucleotide after the polyA tail that is not A. To obtain a cDNA sample representative of the genome adhered to the particles, the primers described above are first adhered to said particles, before reverse transcription. The products of reverse transcription can likewise be adhered to the support after reverse transcription on the support. The grafting can be carried out by biotin-avidin coupling using 5'-biotinylated 5'$(T)_j X3'$ primers, for example 5' $(T)_{19} X3'$ (it is also possible to use chemical complexing between the particles and the targets).

In another embodiment of the invention the primers containing the sequence polyT are mixed Peptide Nucleic Acid-Nucleic Acid (PNA-Nucleic Acid) primers.

FIG. 19 shows an example of carrying out the method according to the invention in which the molecular targets of the mixture are nucleic acids representative of a transcriptome (mRNA), these molecular targets being obtained by a cell lysis step 10.

These molecular targets 12 are combined with the mixed PNA primers 14 Peptide Nucleic Acid-Nucleic acid adhered to magnetic particles. Primers of the (PNApolyT)X type where X is a base chosen from among A, G, and C. Such primers are shown in FIGS. 18d, 18e and 18f. The bond between the PNA and the nucleic acid is made with an ester bond between the oxygen atom in the nucleic acid 5' Phosphate and the terminal COOH group of the PNA. The adherence of the primers to the magnetic particles is achieved for example by attaching a biotin to the terminal NH2 group of the PNA for example and by an interaction with an avidin or streptavidin adhered to the magnetic particles to allow an avidin (or streptavidin)/biotin bond to be made.

Since these molecules have a great affinity for nucleic acids, they bind all the polyA tails of the messenger RNAs in the mixture of targets. The magnetic particles are then immobilised on a support using a magnetic field applied by a magnet 16 or similar to be able to recover the molecular targets 17 that are not retained by the primers.

The reverse transcription 18 of the mRNAs can then be carried out from primers, such as NH2-(PNA-polyT) (X)3' for example NH2-(PNA-T)$_{19}$(X)3' (where X can be an A, C or G nucleotide residue). Another construction, more effective for reverse transcription, consists in using an NH2-(PNA-polyT)XY3' for example NH2-(PNA-T)$_{19}$X(Y)$_2$3' (where Y represents any of the nucleotides A, T, G, C). The reverse transcription is thus carried out starting from the first nucleotide after the polyA tail that is not A.

The complexes formed are then denatured and the magnetic particles are again immobilised by a magnetic field so as to be able to recover the messenger RNA molecules 19. Thus a sample 20 of cDNA representing the transcriptome is obtained adhered to the particles.

Alternatively, using the PNAs to bind the RNA removes the need for the reverse transcription step (steps 18 and 19 in the figure) and so the probes are hybridised directly to the RNAs, which are adhered to the PNAs.

The sample 20 is placed in contact with an array of primary probes 22 which are polynucleotides of which the respective sequences, masses and sizes are known. The polynucleotide sequences are all different, their masses can be identical or different and their sizes can likewise be identical or different.

Each of the polynucleotides carried on the magnetic particles binds specifically at hybridisation with one type of primary probe to make a particle-primer/cDNA-primary probe complex 24. The hybridisation is performed under thermodynamic conditions chosen so that the size of the primary probes has no effect on hybridisation. For this, the temperature of the medium is progressively reduced, following a gentle temperature gradient or for example successively cooling and warming to temperature plateaus, for example the temperature is reduced from a temperature of 70° to a temperature of 40° C. with successive cooling and heating plateau regions (of defined duration that can be from about 10 seconds to several minutes or much more, up to several hours). By way of example, the temperature of 70° C. can be reduced by 3° C. and maintained for time t as a cooling plateau region and then the temperature 67° C. is increased by 1.5° C. and maintained for time t as a heating plateau region. These steps are repeated until the temperature of the medium reaches 40° C.

The primary probes 26 that are not specifically bound to a cDNA are recovered from the mixture as previously described. Next these complexes are denatured then the primary probes 28 representing a fingerprint of the cDNAs are recovered for analysis.

In the case where the primary probes are the same size and same mass, the analysis can be done by hybridising the primary probes to secondary probes immobilised on a support followed by detection of the primary probes by, for example, measuring the change in impedance.

If the primary probes have different sizes and/or masses, the analysis can be done by capillary electrophoresis, chromatography, or mass spectrometry.

In a particular embodiment, each type of primary probe is formed of a polynucleotide (or a polynucleotide portion) capable of hybridising to a particular nucleic acid but resistant to nuclease activity.

This polynucleotide can comprise or consist of a nucleic acid molecule, a PNA molecule (Peptide Nucleic Acid), or a composite mixture of nucleic acid/PNA (FIGS. 18a and 18b), the joining of the two molecules being achieved for example by a PNA cooP(o3) Nucleic acid bond. Likewise the polynucleotide can comprise a nucleic acid of which the sequence has been modified, the first or last residue being for example attached by a thio-diester bond, or a phosphothioate bond, in place of the phosphodiester bond (FIG. 18c).

The polynucleotide sequence of each type of primary probe is specific to a single nucleic acid sequence present in the mixture of molecular targets to be analysed (or, where the targets are not nucleic acids, it can be made to be specifically recognised by a secondary probe). The size and/or the mass of the nucleic acids present in the mixture of molecular targets will be able to be determined from knowledge of the sequences and sizes of the polynucleotides that have hybridised to the molecular targets.

The primary probes can likewise be adhered to magnetic particles, as previously described. In the case where the polynucleotides are mixed composites of nucleic acid/PNA, advantageously the end of the PNA or the thiol will remain free so that the polymer is protected from all enzymatic degradation. The quantity of polynucleotides adhered to the magnetic particles can be larger than the quantity of molecular target expected to be present in the complex mixture. Preferably, the polynucleotide sequences are equimolar.

The primary probes can be constituted of PNAs identifiable by their mass, their size or by chemical modifications (methylation, ethylation, of their bases).

The mixture of molecular targets to analyse is placed in contact with the particles functionalised by the primary probes so that the molecular targets hybridise with the complementary portions of the primary probes. In a particular embodiment of the invention, the particle/primary probe/target complexes are then treated with "endo" and/or "exo" nucleases which will digest the portions of single stranded nucleic acids, such as NF sp. nucleases. Thus all the single stranded nucleic acids are digested. Then the particle/primary probe/target complexes are separated from the enzymes and washed (the enzymes can be inactivated by heat or an inactivator), the complexes are denatured to release the molecular targets in solution, each molecular target being controlled by the size of the primary probe to which it is hybridised.

Each molecular target is then identifiable by its size and/or mass. If a primary probe undergoes a mutation which nevertheless allows it to hybridise to a molecular target (and on condition that the mutation is not at an end of the probe), the observed mass for this molecular target is altered in consequence which allows identification of the mutation or mutations. The complex mixture of molecular targets can be analysed by mass spectrometry or chromatography to identify and quantitate each of the molecular targets.

The functionalised magnetic particles can be re-used to analyse another complex mixture of molecular targets.

This principle can be used in a variation for primary probes made of simple nucleic acid sequences, but then the system (particle-nucleic acid) is more fragile and can only be used once.

When the molecular targets are nucleic acids, each type of primary probe composing the primary probe array is specific and complementary to one type of target within the molecular targets to be analysed.

In the scope of the method according to the invention, applied to nucleic acid molecular targets, the primary probes in the form of a stoichiometric mixture, hybridise under stringent conditions to the nucleic acid molecular targets. These conditions are independent of the probe size.

The hybridisation is performed in thermodynamic conditions, that is to say with a temperature gradient from 90° to 60° C., with successive cooling and heating plateaus (FIG. 1).

To minimise non-specific hybridisation, when the targets and the probes are nucleic acid molecules, the targets and the probes are hybridised in the presence of small nucleotide polymers (X) n where X is A, T, G or C and n varies from 3 to 7 nucleotides, in all sequence combinations possible for n nucleotides, added to the mixture.

In the first instance, the small polymers hybridise to probe and/or target sequences. The probes recognise a specific target, displacing the small polymers to hybridise with said targets.

In a specific example, the probes in the array of primary probes all have a homogeneous size, in particular identical, and each one has a known sequence. The variations in measurement caused by each probe are thus determined.

For example, all the probes in the primary probe arrays have an identical size chosen to comprise between 20 and 150 nucleotides, for example 30, 40, 50 nucleotides or all sizes included within these limits.

In the scope of the analysis according to step d) detection of primary probes eluted after having formed probe-target complexes by nucleic acid sequence hybridisation can be achieved after having performed the following steps:

e. putting primary probes separated and recovered (eluted) in step c) in contact with different types of secondary polynucleotides, each type of secondary probe being able to bind by specific hybridisation with one type of primary probe, f. identification of the molecular targets from the detection, and/or the recovery and/or the analysis of the primary probes hybridised with secondary probes.

These steps can be performed by means of a probe spot matrix, such as that described hereinafter for the 2D electronic chip.

Separation by dehybridisation, of primary probes and nucleic acid molecular targets can be achieved by raising the temperature.

The step of detection and/or recovery and/or analysis of the primary probes recovered after specific binding to the molecular targets, can be performed by mixing the primary probes in contact with the secondary probes immobilised on a support (for example a chip), by simple diffusion of the primary probes or by active mixing, for example by applying electric potentials. Applying electric potentials is done by means of an electrode network.

When detection brings secondary probes into play, it is looking for hybrids formed between primary and secondary probes, for example by measuring the impedance changes caused by the bonds, particularly by the hybridisation of the primary and secondary probes. Measurement of the impedance changes can be done using a device containing a chip (2D electronic chip) such as that described hereinafter.

In the case of nucleic acid molecules, particularly DNA, it is desirable to retain molecular conformation as far as possible, so as to minimise measurement artefacts due to bending of the nucleic acid molecule, and to intra-molecular hybridisations, which lead to variations in impedance similar to those caused by hybridisation. One way of retaining DNA conformation consists in adsorbing it onto an ITO electrode by molecular combing. In particular nucleic acid probes, particularly DNA, are treated as discussed above.

To aid molecular combing of the nucleic acids and their adsorption onto the electrode surfaces, the ITO (or other conductive material) electrodes can be coated with a layer of polyimide (for example Kapton®) (from about 10 to 100 nm thick). The Kapton® layer can optionally be ribbed to better orientate the nucleic acid molecules.

The molecules stretched along the electrode cannot bend or hybridise with themselves. However, they remain able to hybridise with a complementary sequence in solution.

Another answer consists in stretching out the probe molecule (secondary probe) between a functionalised electrode and a non-functionalised electrode, by fixing their ends to the electrodes. The oligonucleotide probes used, are functionalised at both their 5' and 3' ends, the function chosen for the 5' being different to that for the 3'. The two types of functions are different activations and/or catalysis. For example they are chosen from 5' Hs, NH2 groups with chemical or luminescent activation and a 3' pyrrole group for electric catalysis. The distance between the functional and non-functional electrode sets is chosen such that the molecules are stretched out, without taking on a particular bend or allowing intramolecular hybridisation.

An alternative consists in functionalising the 5' end of the probe to join it to the functionalised electrode and adding to it a short 3' sequence (10 to 20 bases) (3' attachment). The sequence of the 3' attachment is chosen specifically so it does not hybridise with the targets. A sequence complementary to the 3' attachment is joined to the non-functionalised electrode facing it. The probes are fastened to the functionalised electrode set by their 5' end using a chemical bond and to the non-functionalised electrode by the 3' end using a duplex, of 10 to 20 base pairs, made between the attachment and the complementary sequence fixed to the electrode. The probes are thus held between two electrodes which minimises intramolecular hybridisation and bending.

The electrode chip with the probes adhered can be passively hybridised by simple diffusion of the probe targets (eluted primary probes making the molecular fingerprint of the molecular targets in the mixture) at each spot, as performed with existing microarrays. However, active hybridisation is preferable.

Once the chip is hybridised, the variation in impedance at each spot allows measurement of the amount of target bound. The intersection between the upper (functionalised) electrode and the intrusion (into the upper level) of a lower (non-functionalised) electrode is unique and corresponds to one single spot. Impedance measurements are performed spot to spot by successively applying an electrical potential difference and an electric current to all the possible electrode pairs formed by one lower and one upper electrode.

Local structural flaws in the materials can cause sporadic resistance between one electrode and the other, leading to artefacts in the impedance readings. Also, functionalisation of the electrodes to adhere the DNA molecules can interfere with the measurement. The use of tin and zinc oxide alloys such as: ITO, ATO, FTO, ZNO (optionally covered with a polyimide or Kapton® layer), minimises these problems. Methods for plating with these alloys are quite standard and reproducible, which produces electrodes with relatively few flaws.

Free molecules are removed by the activity of the electrical fields produced by the electrode network. All the measurements can be done during the hybridisation or complexing reactions using the electrode set which makes it possible to handle all the charged molecules.

With this approach, it is possible to measure the number of secondary probe molecules making up the spot and the number of primary probes which bind specifically, particularly which hybridise. These two measurements make it possible to determine the actual concentrations of the molecular targets initially present in solution. This is because since the size of the primary and secondary probes is precisely measured and identical, and their sequence is known, it becomes possible to normalise the measurement taken, for example the fluorescence measurement, so as to be quantitative.

It is possible to standardise the measurements by producing one chip with identical size secondary probes, or optionally PNA probes. The size of primary probes is normalised to correspond precisely to that of the secondary probes after hybridisation on the chip, by treatment with a nuclease digesting single stranded nucleic acids, as previously described.

The networks are composed of functionalised electrodes made of transparent material such as ITO. This way interfering fluorescence from gold electrodes is avoided. Among the materials that can be used for this connector technology mention can be made of alloys transparent in the visible range such as ITO (indium oxide and tin oxide), ATO, FTO, ZNO or any equivalent alloy. Since these alloys are very electrophilic, they must be insulated (Example 1).

Another method for detecting the primary probe-secondary probe hybrids formed consists in using polarised light filters placed both sides of the chip containing the hybrids (FIG. 2).

A DNA duplex organised in a helix B or in a helix A is chiral with the property of altering the plane of polarisation (oscillation) of light. The angle of deviation $\alpha$ of the light essentially depends on the number of base pairs making up the DNA double helix. The deviation of an angle $\alpha$ is lost when the double helix is destroyed so when a DNA double helix is dehybridised.

This property can be used to quantify the amount of hybridisation at each probe spot on the electronic chip device (Electro Chip) described below.

The ITO electrodes of the electronic chips are transparent, and can be made on sheets of glass, quartz or any other transparent material.

In general terms, an electronic chip is made of a transparent base on which ITO electrodes are deposited, optionally covered in a polyimide layer. On each ITO electrode are adhered probes organised in spots, such that each spot resides in the hollow of a capillary in the associated capillary network. Opposite each electrode adhered to the spots sits an electrode placed on another transparent support. Thus a ray of polarised light with an angle relative to 0° can cross the first transparent support and its electrode, to arrive at a spot. So the light is rotated through an angle of $\alpha°$ by the double stranded DNA molecules (hybridised molecules) and comes out through the electrode and transparent base opposite. The amount of light subjected to a deviation of $\alpha°$ is exactly proportional to the number of hybrids making double helices on the spot, and so precisely proportional to the quantity of targets hybridised to the probes.

The light deviated by an angle of $\alpha°$ is analysed as it leaves after having crossed the second electrode and second transparent base.

To obtain light polarised at 0° (an arbitrary origin which can be changed to another specified origin), a filter polarised at 0° is placed on the external face of the transparent support on which the electrodes are fixed.

A second polarised filter orientated at $\alpha°$ is placed on the external face of the other transparent electrode support opposite (cf. diagram). The light comes from a visible spectrum laser or any other source of white light.

In general terms, all light for which the support is transparent, and which the probes and targets do not absorb, can be used. This detection method can be applied to conventional nucleic acid chips confined between two plane polarising filters for which the planes of polarisation are staggered with an angle between them of $\alpha°$.

The two polarising filters can move with respect to each other so as to increase the detection efficiency, modifying the angle between the two planes of polarisation. This change of angle allows measurement of different deviations of the light and so the measurement of the homogeneity of target sequences (primary probe-secondary probe) hybridised at one spot. It is thus possible to determine the target polymorphism.

This is because the differences in sequence between the target (here the primary probe) and the probe (here the secondary probe) lead to mismatches that in places fold the double helix formed, thus altering the chirality of the molecule. Thereby, the angle of light deviation is modified as a function of each chirality. The measurement of each angle gives information on each of the populations.

In another example of a specific use, detection of bonding at hybridisation between primary probes and secondary probes can be done by detecting the fluorescence of a ligand in the double strand hybrids formed between the primary probes and the secondary probes or of a single stranded nucleic acid ligand. At least one detector is used to measure the intensity of fluorescence produced by the hybridisation of primary and secondary probes.

Without labelling the primary probes, the amount of primary probe-secondary probe complexes formed on the chip can be measured using the fluorescent ligands. For DNA chips, acridines can be used and particularly acridine orange which is positively charged and intercalates in DNA. Acridine orange permits differential labelling of single stranded or duplex double stranded DNA.

In another specific example, detection of primary probes hybridised to secondary probes is done by PSR adapted for the 2D electronic chip described hereinafter. At least one detector is used to measure the hybridisation of primary and secondary probes by PSR.

The targets constituted by primary probe/secondary probe complexes can be directly quantified with the network of functionalised electrodes. A trihedral prism is fitted to the back of each line of electrodes in the network of functionalised electrodes to allow PSR measurement.

Another aspect of the invention concerns the carrying out of the method described above, for the analysis, and quantification of molecular targets in a complex mixture when the targets are polypeptides or other targets able to form specific complexes of the receptor-ligand type.

The embodiments of steps a) and b) of the method described above in particular for the detection of nucleic acid targets are in principle applicable. Thus, polypeptide targets in the complex mixture to be analysed can be adhered to particles (magnetic or otherwise, of one or more types), and brought in contact with the primary probes in solution. For example it would be possible to use ITO coated magnetic beads. If different types of proteins are analysed they can be adhered to different types of particles.

As indicated above, the array of primary probes used incorporates probes comprising a polypeptide portion and a polynucleotide portion. Quantification of molecular targets specifically bound to the probes of the primary probe array is performed after recovery of the polynucleotide portions of the probes in the probe-target complexes.

Since the polypeptide portions and the polynucleotide portions of each type of probe are specific to a single type of target, the identification and quantification of the polynucleotide portions of the probes is indicative of the presence and quantity of the molecular targets.

According to the terms and conditions described above, the polynucleotide portions of the probes have different masses and/or sizes and identical or different sequences or different sequences and homogeneous or identical sizes among the probes. The differences in question make it possible to choose an appropriate detection system. Thus, the polynucleotide portions can be detected for example by any means able to show their differences in sequence (hybridisation with secondary probes), size (electrophoresis, chromatography) or mass (mass spectrometry).

When the targets are proteins, the primary probes are compounds having the ability to bind specifically to the targets, for example antibodies or functional antibody fragments comprising in or containing the antigen binding site, or receptors having an affinity for the target proteins.

In a specific example, the primary probes comprise a portion constituted by a polynucleotide adhered to the portion of said compounds having a specific affinity for the target proteins. This polynucleotide constitutes a label in the sense of an identifier (otherwise known as a tag) specific for each compound. Such polynucleotides are illustrated in the examples. Their use makes it possible to detect the primary probes separated after they have bound the proteins.

In this aspect of the invention consisting in detecting polypeptide molecular targets, for example in a proteome, step a) of the method according to the invention consists in for example placing in contact the mixture that may contain proteins for analysis conforming to the present description, with an array of different types of primary probes, composed of an array of monovalent antibodies or fragments of monovalent antibodies comprising in or containing a single antigen binding site for example Fab fragments or any molecule formed from all or part of the variant chains so that they contain a single antigen recognition site) each binding to a specific nucleic acid sequence called a sequence tag, each type of antibody or antibody fragment in the array being capable of making a specific bond with a single type of protein to be analysed, under conditions allowing specific binding of said proteins and said antibodies or fragments of antibodies.

When the targets are proteins, the separation at step c) of complexes formed by the binding of primary probes and targets can be achieved by enzymatic methods known to those skilled in the art. In a specific example, step c) of the method according to the invention comprises separating the proteins and antibodies or fragments of antibodies joined by a specific bond, then separating each sequence tag of the antibody or antibody fragment that matches it, so as to recover the array of sequence tags representing a fingerprint of the bound targets selected from among the proteins to be analysed.

Step d) of the method according to the invention comprises identifying the proteins from the detection, and/or recovering and/or analysing the tags distinguishable by their sequence the tags being of identical size, or on the contrary by their different sizes and/or masses.

In a specific example, when the tags have different sequences but identical sizes, they are detected using the same methods as those described above for nucleic acid molecular targets. In particular secondary probes specific to the tags are used.

So the characteristics of the tags are the same as those described above for polynucleotide primary probes intended to hybridise with nucleotide targets.

When the primary probe array consists of probes for which the polynucleotide portions have a different mass, the array can be constituted in such a way that it comprises over 10, particularly over 50 over 100 or over 1000, or even over 10 000 or 20 000 probes of which the polynucleotide tags all have different masses, for example 30, 40, 50, 100, 500, 1000 2000, 5000 or more, or a number of probes included in an interval formed by values falling between two of these limits.

Detection of the tags (a probe being identified by one tag and only one) can be achieved by any method of mass detection for example mass spectrometry.

In another specific example, the tags (a probe being identified by one tag and one only) are analysed by means of their size differences. So detection can be by electrophoresis or chromatography.

Further, these tag sequences can be chemically modified by adding methyl or ethyl groups to the bases in the residues, so that it is possible to identify the primary probes by their masses or by their chemical modifications, in accordance with what has been described above.

It is possible for example to identify tag sequences and the primary probe polynucleotides in general by their retention time during gaseous phase or liquid chromatography and to quantify them by optical absorbance, natural fluorescence of the nucleic acids, or by measuring the phosphorous in the plasma produced at the end of chromatography (by phosphor fluorescence or mass spectrometry).

So the primary probe array is constituted in such a way as to have over 10, particularly over 50 over 100 or over 1000, or even over 10 000 or 20 000 probes of which the polynucleotide tags are all of different sizes, for example 30, 40, 50, 100, 500, 1000 2000, 5000 or more, or the number of probes included in an interval formed by values falling between two of these limits.

A further object of the invention is a device for implementing the method described.

A device according to the invention consists, for example, of:
  optionally a set of particles, for example magnetic particles, that can strongly bind the molecular targets of nucleic acids and/or proteins of the mixture to be analysed;
  an array of primary probes of different types corresponding to the description given in the present request, in the form of a stoichiometric mixture, in solution or able to be dissolved for use, said probes being made of a polynucleotide or comprising a polynucleotide specific to each probe, each type of primary probe composing the array is able to bind by a specific bond to one type of molecular target to be analysed, when said primary probes and said molecular targets are put into contact, and if necessary,
  means for separating and means for recovering the primary probes and the molecular targets bound by specific bonds, so as to obtain an array of primary probes representing a fingerprint of the molecular targets to be analysed and/or if necessary,
  an array of secondary probes capable of specifically recognising the polynucleotide portions of the primary probes of the array of primary probes and/or if necessary,
  an oligonucleotide micro-array (for example of the 2D electronic chip type) in which the oligonucleotide probes (composing the array of secondary probes) of each spot comprises a complementary sequence of a primary probe type sequence or of each tag.

In the context of nucleic acid analyses, the means of separating, and particularly for dehybridising the primary probes and the molecular targets can be means that increase the temperature, so as to separate the two strands of the hybrid.

In the context of protein analysis, the means for separating the primary probes from the molecular targets can be particularly reagents for carrying out enzyme separations.

The means for recovering the primary probes separated from the molecular targets can comprise magnetic particles on which the targets are immobilised and a means capable of generating a magnetic field within the solution containing said primary probes and said targets.

The means for recovering the primary probes separated from the molecular targets can comprise particles on which the targets are immobilised and a means of causing centrifuging within the solution containing said primary probes and said targets.

The method can take different forms to be used for measuring the concentrations of different proteins and their modifications in a mixture taken for example from a cell extract.

When the molecular targets are proteins, the device consists of, by way of illustration:

1) A set of particles (particularly magnetic or a surface) that can strongly bind the proteins of the mixture to be analysed containing the targets. Typically, mention can be made of polystyrene, nylon, nitrocellulose, etc. beads or membranes.

2) A stoichiometric mixture of primary probes consisting for example of monovalent antibodies or of fragments of antibodies comprising a single antibody binding site, in which each type of antibody is bound strongly (for example covalently) to a specific sequence of nucleic acid or polynucleotide (the sequence tag). The sequence tag breaks down for example into one or two generic sequences that can be cut specifically and a unique and specific sequence for each type of antibody or fragment of antibody described above; and optionally, 3) An oligonucleotide chip, in which the oligonucleotide probes (composing the array of secondary probes) of each spot comprise a sequence complementary to the specific part of the sequence tag of one of the types of antibodies of the stoichiometric mixture of antibodies.

For quantitative analysis, it is indispensable that each probe should contain a single binding site to one target and a single polynucleotide tag. The antibodies or their fragments such as the Fab fragments are suitable because they have a binding site that can be associated with a tag.

By way of example, starting from a cell extract, the proteins are bound to magnetic polystyrene particles. The polystyrene has the faculty of durably adsorbing proteins, particularly hydrophobic proteins. An excess of beads is used compared with the concentration of proteins to avoid saturating the beads, thus limiting the steric hindrance. Depending on the desired study, proteins can be denatured or not. The beads and the bound proteins are then:
  1) precipitated by a magnetic field,
  2) isolated from the supernatant,
  3) washed and recovered in a saline buffer.

The beads are then saturated with proteins that are inert for the system studied. For example, bovine serum albumin (for studies on target molecules that are not of bovine origin), small size proteins exogenous to the species studied (such as Kunixt inhibitor) or else aliphatic chain amino acids (such as leucine) are used. Steps 1 to 3 are carried out again. Then the complete system of saturated beads-bound proteins is put with the equimolar mixture of antibodies carrying the sequence tags to form a complex. The antibodies bind specifically to their target proteins immobilised on the beads. The quantity of each type of bound antibody is proportional to the quantity of each type of protein adsorbed onto the beads.

In order to decrease the steric hindrance, but above all to allow for quantification, the antibodies must be monovalent or must be substituted by monovalent antibody fragments (or half-antibodies) for example obtained by enzyme digestion, particularly by papain, or synthetic or recombinant fragments. Each half-antibody is "tagged" with a nucleic acid sequence. Steps 1 to 3 are carried out again. The antibodies (or half-antibodies) which have reacted are thus isolated and separated from those which have not reacted. The nucleic acid tag is cut off using the cutting sequence introduced. This can be a palindromic sequence, for example, or the target sequence of an abzyme . . . . In the case of a palindromic sequence, two particular solutions may be mentioned:

The palindromic sequence is introduced between the antibody and the specific sequence tag. In order to separate the sequence tag from the antibody, a sequence is simply added to the medium which is complementary to the cutting sequence with the corresponding restriction enzyme, which makes it possible to separate the antibody from the specific sequence tag.

Two cutting sequences are introduced respectively between the antibody and the specific sequence tag, and at the end of the sequence tag, such that these two sequences are complementary to each other. In hybridising, they form the specific cutting site for an enzyme which is subsequently introduced into the medium. The specific sequence tags are then released into the solution.

Once they are separated from the antibodies, the sequence tags supply a mixture of oligonucleotides in solution the quantities of which are proportional to those of the types of antibodies retained on the beads, and thus proportional to the different proteins and to their modifications present in the cell extract analysed. The mixture of nucleotides obtained can be analysed on a conventional DNA chip or a chip as previously described.

In the case where the array of primary probes (comprising a polypeptide portion and a polynucleotide tag) comprises a large number of different types of primary probes, the sequence tags need to be large and include chemical modifications in order to be able to differentiate them. However, the large size of the sequence tags and their modifications may hinder the binding between the primary probes and the molecular targets by masking the binding sites. Moreover, it is very difficult to graft nucleotide sequences of more than 20 bases onto an antibody or a Fab antibody fragment efficiently.

In order to work around this problem and as shown in FIG. 20, the tag sequences comprise about 10 to 20 bases (preferably 18), which makes it possible to generate between $4^{10}$ and $4^{20}$ different sequences. In order to recognise the tags, mixtures of equimolar probes are prepared known as "report probes" in which each report probe is comprised on the one hand of the sequence complementary to the tag of one type of primary probe, and on the other hand of a sequence of variable size that does not recognise any sequence tag. Each report probe is defined in such a way that it is recognised unequivocally by its size and/or mass, and/or by its chromatographic properties, as described above.

FIG. 20 illustrates an example of an embodiment of the method according to the invention in which the molecular targets of the mixture are proteins representative of a proteome, these molecular targets being obtained by cell lysis step 40.

These molecular targets 42 are mixed with particles 44 capable of binding the molecular targets as described above. The particles are immobilised on a support using a magnetic field applied by a magnet 46 or analogue in order to remove the molecular targets 48 which are not bound to a particle.

The molecular targets 42 are then mixed with the primary probes 36 so that the molecular targets bind specifically to the primary probes to form particle/molecular target/primary probe/report probe complexes 50.

After eliminating the primary probes 52 that are not specifically bound to a molecular target, the particle/molecular target/primary probe/report probe complexes are isolated and denatured and the report probes 54 that have dissolved are isolated from the particle/molecular target/primary probe complexes. The report probe composition of the solution represents a fingerprint of the molecular targets retained on the particles, and the composition and quantification of the mixture is carried out for example by mass spectrometry, chromatography, chip reading, etc.

As a variant, instead of putting the report probes in contact with the primary probes, they can be put in contact with the particle/molecular target/primary probe complexes so that the report probes hybridise with the corresponding tags of the primary probes and saturate them.

The tags may advantageously be molecules of PNA the sequences of which are known and which are attached at their $NH_2$ extremities to the COOH extremities of Fab fragments of antibodies by peptide bonds.

The invention also relates to a device for carrying out step d) of analysing the primary probes recovered in step c) of the method for analysing molecular targets according to the invention, following the various embodiments described in the previous pages, consisting of:
- a capillary network allowing the primary probes to circulate,
- a matrix of secondary probes organised in spots, the matrix being disposed in such a way that it is in contact with the capillary network,
- a network of electrodes, known as functionalised electrodes, onto which the secondary probes are bound, this network being set out in such a way that each line of spots of the spot matrix is bound to one of the functionalised electrodes of said network.

The device is implemented after having carried out the steps of specific binding of the molecular targets with the primary probes and after having separated the primary probes in the complexes formed in making the fingerprints of the molecular targets.

This device is for example a chip known as a 2D electronic chip, such as described above, in which the chip comprises a two-dimensional matrix of biological probes (array of secondary probes) organised in spots, associated with at least one array of electrodes. The matrix is contained in a network of parallel capillaries interconnected by two reservoirs (one at each of their ends).

The term "capillary" as used herein is understood to mean any appropriate canal that allows fluids to circulate, with a diameter of under 1 millimetre, preferably comprised between 1 and 100 µm.

The capillary networks are for example bored or moulded in materials such as silica, quartz, plastics (Plexiglas for example), PDMS, using acid etching techniques for silica or laser machining for plastics, known to those skilled in the art.

In a preferred embodiment, each capillary network is bored in the thickness of a plate of appropriate material.

Generally, capillary networks can be filled with gel such as a polyacrylamide gel or any other gel that makes it possible to regulate and control the diffusion of primary probes during their migration, particularly liquid gels used for capillary electrophoresis.

The primary probes can be contained in a solution or in a fluid, said fluid or said solution circulating in the capillaries.

In a specific example, the device comprises a transversal capillary, called the transversal canal, in which the primary probes are placed which have hybridised with the targets, the diameter of this canal being preferably comprised between 2 and 1000 µm. The upper transversal canal is connected to the capillary network.

The device also comprises a matrix of secondary probes organised into spots, where each spot is made up of one type of molecular probe, for example a nucleic acid polymer the sequence of which is strictly complementary to the sequence of one of the primary probes contained in the array of primary probes.

The matrix of secondary probes may be placed on or fixed to the capillary network.

The first array of functional electrodes has grafted electrodes of secondary probes organised in spots, each secondary probe being capable of retaining one specific primary probe, by a specific probe/probe bond.

Each line of spots of the matrix is deposited on a gold or ITO surface (or any other appropriate metal or alloy) delimiting an electrode, the whole of the matrix then consisting of n electrodes corresponding to the number of lines n, each electrode line consisting of P spots of grafted electrodes (FIG. 3).

Since ITO is very electrophilic, it is necessary to insulate by an encapsulation process the portions of the electrodes which have not had probes grafted on, in order to avoid any non specific capture of targets or primary probes. For example, a polypyrrole film can be used. The film is created by passing a current through the grafted electrodes in the presence of a pyrrole solution. Pyrrole polymerises spontaneously with the action of the current and insulates the free portions of the electrodes. The electrodes can also be saturated by a small oligonucleotide which cannot hybridise in a stable manner with the targets, for example an ATA or TAT, etc. trimer.

The probes (spot or hybridisation units) are deposited depending on the case on the electrodes or between the electrodes.

The electrodes are etched in thin layers on an insulating material such as glass, polyimide (for example Kapton®), or alumina oxide.

Any appropriate method for attaching the secondary probes can be used. By way of example, particular mention can be made of the covalent pairing of the biotin-avidin type between molecular probes paired with biotin and beads functionalised with avidin, such as those marketed by "DYNAL" (Dynal distributors Worldwide, copyright 1996 Dynal AS—Technical Handbook second edition).

In general, all types of pairings, for example chemical bonds, strong interactions, described for chromatography columns may possibly be suitable.

For example, the interactions used currently in DNA chips for binding nucleic acid probes, or protein chips for binding polypeptide probes can also be adapted (electrostatic lysine/nucleic acid interaction, silane binding, pyrrole polymerisation on the surface of the lodge, etc.), as can in situ synthesis methods on the substrate. It is also possible to envisage the use of nylon or nitro-cellulose to bind the probes irreversibly to the substrate. The binding can be direct or can be done via a bridge such as a psoralene bridge between a particle of nylon and a secondary probe.

The secondary probes much be attached sufficiently strongly to the electrodes to resist the different treatments applied and to resist any electric fields used to manipulate the targets.

In a specific example, the binding of the secondary probes onto the electrodes resists the different most widely used denaturing treatments, which makes it possible to regenerate the chip after use.

In a specific example, the device also comprises a network of so-called non-functionalised electrodes, this network being disposed in such a way that the capillary network is situated between the two electrode networks.

These electrodes are called non-functionalised because they have no probes grafted onto them.

In a specific example, the device making it possible to analyse molecular targets measures the variations of impedance related to the hybridisation of primary and secondary probes.

In a specific example, the device measures the variations of light polarisation related to the hybridisation of primary and secondary probes.

In a specific example, the device also comprises a detector that measures the intensity of fluorescence related to the hybridisation of primary and secondary probes.

In a specific example, the device measures the hybridisation of primary and secondary probes by PSR.

The electrodes can be etched in a thin layer on an insulating material.

The two electrode arrays are set out opposite each other on each side of a network of P parallel capillaries, such that there is one array of electrodes above and another below (FIGS. 4 and 5).

In a specific example, the array of functionalised electrodes is situated above the capillary network and the array of non-functionalised electrodes is situated below the capillary network.

In a specific example, the array of functionalised electrodes is situated below the capillary network and the array of non-functionalised electrodes is situated above the capillary network.

Each capillary is perpendicular to the n electrodes of the array of functionalised electrodes and to the n electrodes of the array of non-functionalised electrodes (FIGS. 5, 6 and 7).

Each spot of functionalised electrodes is in each capillary of the capillary network.

The construction is carried out in such a way, that the first spot of the n functionalised electrodes is in the first capillary of the capillary network, the second spot of the n functionalised electrodes is in the second capillary of the capillary network, and so on (FIG. 7). An electrode pair comprises one electrode grafted with probes organised in spots above the capillary network and one non-functionalised electrode opposite below the capillary network. The electrodes can be very thin to allow detection by PSR.

At each end of the capillary network, the capillaries converge towards a circular reservoir. The reservoir comprises one electrode (reservoir electrode), in the same plane as the array of functionalised electrodes (FIG. 7). In a specific example, this electrode is circular. In a specific example, this electrode is situated in the centre of the ceiling of each reservoir.

The device according to the invention can also comprise a first and a second supplementary link electrode situated respectively between the first reservoir electrode and the first functionalised electrode, and between the second reservoir electrode and the last functionalised electrode, such that the shortest distances between each link electrode and the corresponding reservoir electrode are identical at all points of the electrodes.

The link electrode can be curved, its curvature being defined such that the distances between each link electrode and the centre of the reservoir (reservoir electrode) are identical at all points of the electrode.

The second reservoir can be formed by at least one transversal canal, called the lower transversal canal, which is connected upstream of all the capillaries of the capillary network and downstream of the detector. The primary probes which are hybridised to the secondary probes can be separated and put into circulation until they reach the detector, in particular by the lower transversal canal.

In the context of a chip in which the secondary probes are put into circulation until they reach the detector in order to be analysed, it is necessary to alternate one functionalised electrode and one non-functionalised electrode in the construction of the electrode network.

The device according to the invention allows for a specific direct bond, in particular a direct hybridisation of the primary probes which are specifically linked, particularly hybridised to the molecular targets.

In a specific example, this hybridisation of the primary probes circulating through the matrix of secondary probes is carried out as follows:

1) the eluate of primary probes to be analysed is introduced into the first reservoir. An electric potential is applied between the first curved electrode (positive) and the electrode of the first reservoir (negative). The primary probes migrate in equimolar fashion in each of the capillaries and become concentrated at the curved electrode.

2) the potential applied between the reservoir electrode and the curved electrode is cut and an electrical potential is applied between the first functionalised electrode (+) and the curved electrode (−). The probes of each capillary then migrate to the first functionalised electrode where the secondary probes complementary to the spots of the first electrode (one spot per capillary) hybridise (the hybridisation is accelerated by the electric field). The concentration at each spot is maximum (it only depends on the number of capillaries and no longer on the total volume of the canals). In order to confine the primary probes to the spot, the second electrode in the functionalised line can be given a negative potential, which leads to obtaining a charge distribution (−+−) where the +charge is centred on the first spot of each capillary.

3) in order to improve the hybridisation, the electric potentials can be discontinuous, the time lapse with no potential corresponding to a time of relaxation, during which the primary probes can hybridise without constraint. In order to increase the mixture of primary probes and so encourage hybridisation of the primary probes present in small numbers, during the time of relaxation a discontinuous and alternating potential can be established between the first electrode in the functionalised line and the non-functionalised electrodes above and below the capillary network (this further improves the specificity of hybridisation).

Once the primary probes are hybridised at the first line of the spots, the electrical potentials are moved to the next line. By calling the position of the curved electrode 0 and the positions of the first, second and third functionalised electrodes grafted with probes 1, 2 and 3 respectively, the kinematics of the applied electrical potential can be described as follows:

4) the second functionalised electrode is put at a positive potential, the charge distribution is then (0−, 1+, 2+) (optionally the third electrode is put at a negative potential) with a charge distribution (0−, 1+, 2+, 3−);

5) the first functionalised electrode is put at a negative potential. The charge distribution is then (0−, 1−, 2+) optionally (0−, 1−, 2+, 3−).

6) The curved electrode is put at 0 for a charge distribution (1−, 2+) optionally (1−, 2+, 3−).

7) A discontinuous alternating potential is applied between the array of non-functionalised electrodes and the functionalised electrode 2.

All the non-hybridised probes at the first line of spots will migrate to the second line of spots (FIG. 8). The whole kinematics of migration, relaxation, mixing (corresponding to steps 4-7 above) is applied from one line to the next to hybridise all the spots of all the lines which have complementary primary probes in the sample analysed. Once they have arrived in the second reservoir, the primary probes which have migrated in the different capillaries mix once again. It is then possible to carry out the electrical potential sequences in the other direction to navigate through the capillary network in the reverse order. The shuttling back and forth of the primary probes between the two reservoirs through the capillaries increases the detection sensitivity of the device.

As a general rule, electric fields of the order of 160 mV/mm have to be applied to move the molecules effectively. Since there is a large distance between the curved electrode and the reservoir electrode, the potentials applied to these electrodes in order to respect the field are of the order of a volt, and no longer a millivolt. To avoid the curved electrode and the reservoir electrode burning, it is preferable to make them in gold.

In a specific example, one of the networks of electrodes is formed by superimposing two perpendicular arrays of electrodes in two different planes, and the other electrode network is then earthed. The spots are grafted onto the electrodes of the lower array at the intersection of the intrusion of the electrodes of the upper array into the plane of the lower electrodes.

In a specific example, the functionalised electrode network is formed by a square mesh pattern of lines and columns of electrodes in which, at each intersection between a line electrode and a column electrode, a spot electrode is connected to a line and a column by a field effect transistor.

The perpendicular layout of the two superimposed arrays of electrodes makes it theoretically possible to take measurements. However, the use of an alternating or discontinuous current and the fact that one electrode connects several spots leads to problems of parasite electrical capacity which interfere with the measurement. In fact, it becomes difficult or impossible to measure the electrical current and voltage correctly to define the impedance of each spot. In order to overcome this problem, switches need to be introduced to create a spot to spot voltage and current.

In order to create switches that are compatible with microarray dimensions, the array of functionalised electrode is replaced by a mesh pattern of electrodes in the same plane, comprised of a first set of electrodes (horizontal or in lines) insulated and perpendicular to a second set of electrodes (vertical or in columns). The square of the mesh defines a space into which a small electrode (spot electrode) is placed measuring 10 to 500 μm in length depending on the size of the mesh. Typically, each square of the mesh has a height h of about 150 μm and a width l of about 500 μm. One or two field effect transistors are placed in each square of the mesh, so that the transistor grid is connected to the horizontal electrode on one side of the square, the transistor input terminal (source) to the vertical electrode of one side of the square and the output terminal (drain) of the transistor to the spot electrode (FIG. 9a).

In the variant represented in FIG. 9b, each square of the mesh comprises two spot electrodes O each of which is associated with a transistor FET 1 and FET 2, the second transistor FET 2 acting as a detector. The grid P of the first transistor is connected to a first line electrode M and the grid P of the second transistor is connected to the second spot electrode. The sources Q of the two transistors are connected to the same column electrode N on one side of the square. The drain R of the first transistor FET1 is connected to the first spot electrode and the drain R of the second transistor is connected to the second line electrode M which is independent from any other transistor.

In this configuration, the line electrodes of the mesh are doubled. The first of the line electrodes M connects the grids P of the first transistors FET 1 of a line of the mesh and the second line electrode M connects the drains R of the transistors FET 2 of this line of the mesh.

After hybridisation each transistor FET 1 is used to apply a voltage to the spot electrode to which it is connected. An alternating or direct electric current or electric potential is applied to the source Q of the transistor FET 1. The electric potential or the variation of electric potential applied creates currents and potentials locally at the nucleic acid molecules grafted on the spot electrodes. This is because the molecules grafted onto the two spot electrodes of a square of the mesh behave like little electrical capacitors. The variations in the current or potential at the grid P of the transistor FET 2 change the state of closure of this transistor leading to proportional variations in current and potential between the source Q and the drain R of the transistor FET 2. These variations are contingent on the sequence, size and state of hybridisation of the molecules grafted on the spot electrodes. In particular, these variations are contingent on the single or double stranded state of the nucleic acids and so they make it possible to quantify the degree of hybridisation at each spot electrode.

The use of two spot electrodes in a square of the mesh makes the measured signal and the sensitivity of this measurement strongly contingent on the shape of these two spot electrodes. The measurement can be improved by using spot electrodes in nested spirals or by putting onto the upper plate a counter-electrode made of insulated spot electrodes, images of the spot electrodes of the first matrix.

Another solution consists of separating this mesh with two transistors per square into two meshes with a single transistor per square, these meshes being situated one on each side of the capillary network.

The first mesh known as the control shown in the lower right-hand corner of FIG. 9c is identical to that in FIG. 9a. It stretches below the capillary network and allows for a selective supply to each spot electrode. The column N and horizontal M electrodes are electrically insulated and the spot electrodes O are covered with a 10 to 40 nm thick polyimide film for grafting molecules.

The electrical measurements are carried out by a second mesh shown in the upper right-hand corner of FIG. 9c which stretches above the capillary network facing the first mesh. This mesh makes it possible to control the migration and confinement electric fields of the probes placed in the capillary network for hybridisation. For this, the column electrodes N (or inversely the horizontal electrodes M) and the spot electrodes of this mesh may not be electrically insulated. For each transistor FET 2, the source Q is connected to a column electrode, the drain R is connected to a line electrode, and the grid is connected to a spot electrode. The line electrodes M are covered by the capillary walls (or inversely the column electrodes N).

Once the chip is hybridised, each spot electrode O of the control mesh (FIG. 9c) is switched on in sequence (alternating field and current). The current between the source Q and the drain R of the transistor FET 1 of a spot electrode depends in its intensity, voltage, frequency and phase difference on the state of hybridisation of the probes grafted onto the spot electrode. The current and the voltage produced at the spot electrode of the control mesh opens proportionally the grid P of the transistor FET 2 of the spot electrode situated opposite in the detection mesh, which creates a measurable current and voltage between the source Q and the drain R of the transistor FET 2 of this spot electrode.

To summarise, a mesh is obtained such that the squares, defined by the horizontal and vertical electrodes, are occupied by small spot electrodes. The spot electrodes are connected to two of the four sides of the square by one or two field effect transistors. The molecular probes are grafted at each spot electrode. The electrodes of the upper set are placed opposite each column of "spot electrodes" and parallel to the vertical electrodes of the lower mesh. Each electrode in the lower set is earthed. The set of non-functionalised electrodes can be replaced by a single earthed plate, or a detection matrix such as described above or a matrix of insulated spot electrodes.

By switching on the horizontal electrodes, the grids of all the transistors are powered, which cuts off the current between the input and the output of all the transistors; the spot electrodes are then insulated. By cutting the current of a single horizontal electrode and applying the current and an alternating electric field to a single vertical electrode, only the transistor at the intersection of the two electrodes allows the current to flow between their input and output. A single spot is switched on, so the variation of impedance at the spot electrode can be determined without any parasite effect from the other spots.

In a particular embodiment, the grid operation is reversed for the transistor, that is to say that the current only flows between the source and the drain if the grid is switched on. In these conditions, the lines are controlled by switching on the grid electrodes.

In a specific example, step c) of the method according to the invention is carried out inside the reservoir of the capillary network of the device according to the invention.

The group of "magnetic beads-primary probes-molecular targets" is denatured in a controlled fashion, in the desired volume, in order to recover the eluate containing the primary probes which have previously bound specifically, in particular which have hybridised.

It is then possible to introduce a magnetic field in a reservoir which will receive the target/primary probe complexes bound to the beads. This can be either a static micro magnet fixed to the wall of the reservoir opposite the reservoir electrode, or a solenoid obtained by depositing a thin layer on the same wall (the magnetic field being produced by an alternating current in the solenoid).

The magnetic field makes it possible to keep the particle-molecular target group inside the reservoir. The temperature of the system is increased in order to separate, for example to dehybridise, the primary probes and the targets. The overall temperature of the system is regulated by a water bath or in a warm room and optionally, local regulation is obtained by electrical resistors placed in the reservoirs.

The solenoid has a double use as a magnetic field generator and as a heating resistor.

Once the primary probes are denatured and in solution in the reservoir, they move into the capillaries and bind, particularly they hybridise to the spots.

The temperatures of the thermostat system must be adjusted to allow the primary probes to hybridise to the spots. Chemical denaturing of the primary probes on the beads can be carried out. In these conditions, the beads need to be removed with the magnet after the hybrids are denatured and the primary probes have migrated to the curved electrode in the reservoir. To allow hybridisation, the medium must be neutralised.

The present invention also relates to an array of primary probes representing a replica of the molecular targets to be analysed comprising:

an array of primary probes of different types, as described above, means for separating and means for recovering the primary probes and the molecular targets bound by specific bonds, so as to obtain an array of primary probes representing a fingerprint of the molecular targets to be analysed.

Subject to their technical compatibility, the characteristics described in this request above can also be combined with different characteristics described in the examples, such that other particular embodiments of the invention can be described.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Cross-section at the spot electrode of a 2D electronic chip.

In order to graft the probes a grafting guide is used to guide and orientate the grafting on the electrode.

The grafting guide is obtained either by rubbing the material constituting the guide with a piece of velvet, or by moulding the material to be used to make the guide with short fragments of single stranded DNA deposited and combed onto the spot electrode. The guides are then obtained after abrasion of the material and/or elimination of fragments of DNA.

Figure 1:
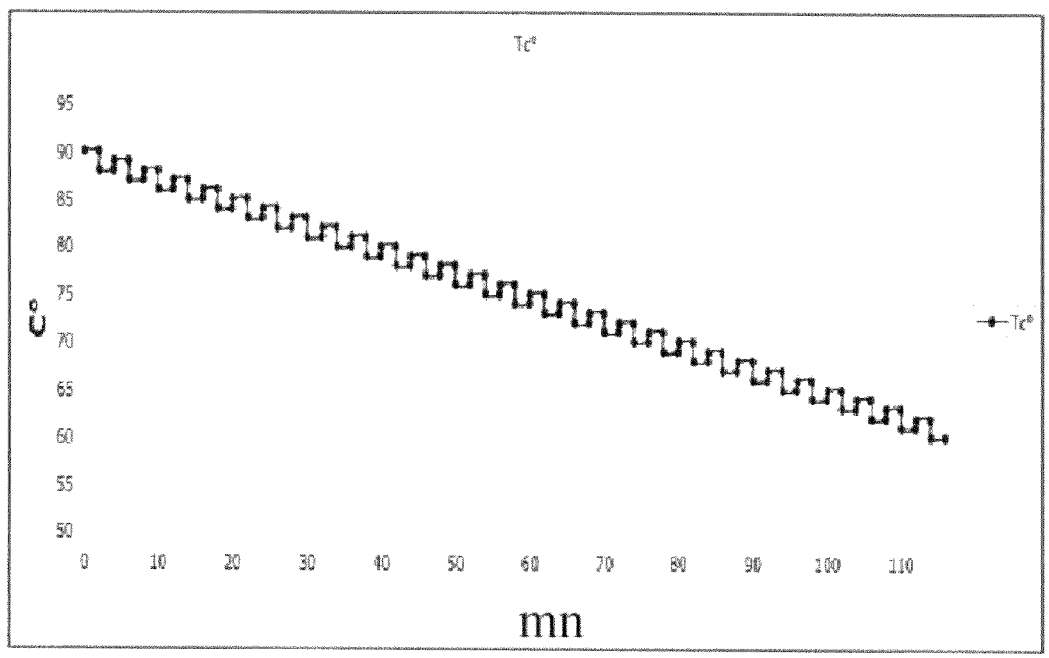
FIG. 1 shows an example of temperature variation applied during probe target complexation (hybridisation) to make the recognition more specific between the probes and the targets.
Figure 2:
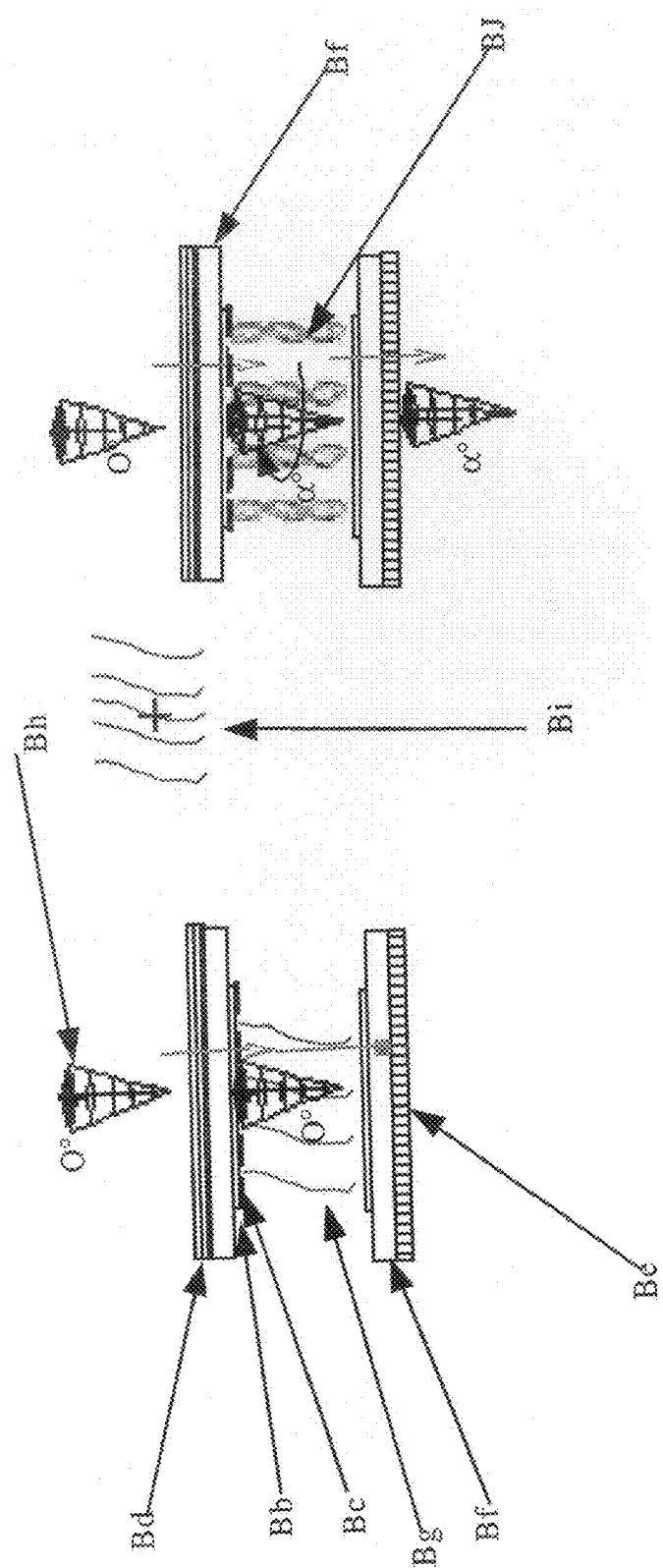
FIG. 2 shows a polarised light detector.
Figure 3:
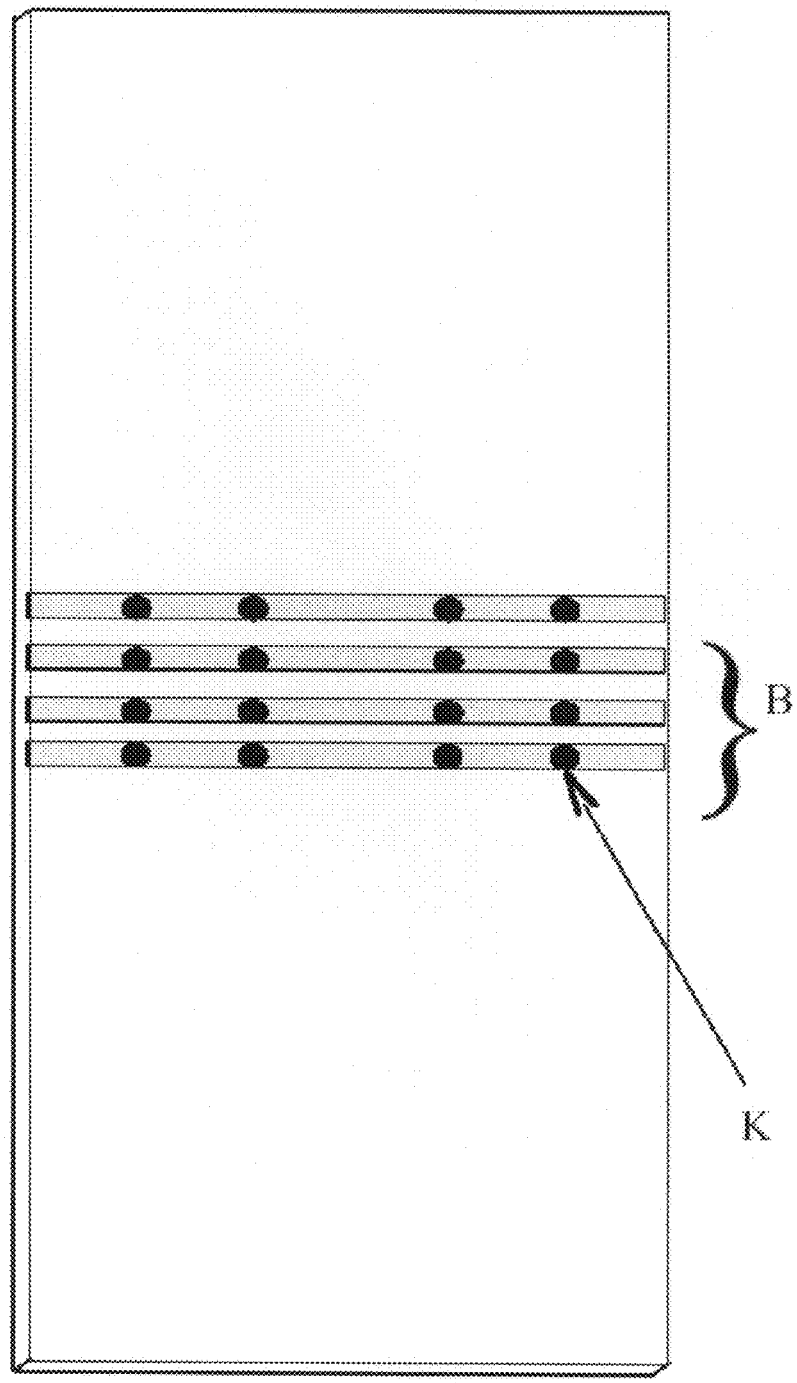

FIG. 3 shows an example of a set of functionalised electrodes grafted with probes. The gold or ITO electrodes are etched on a glass slide; probes (spot or hybridisation unit) are deposited on the electrodes.

Figure 4:
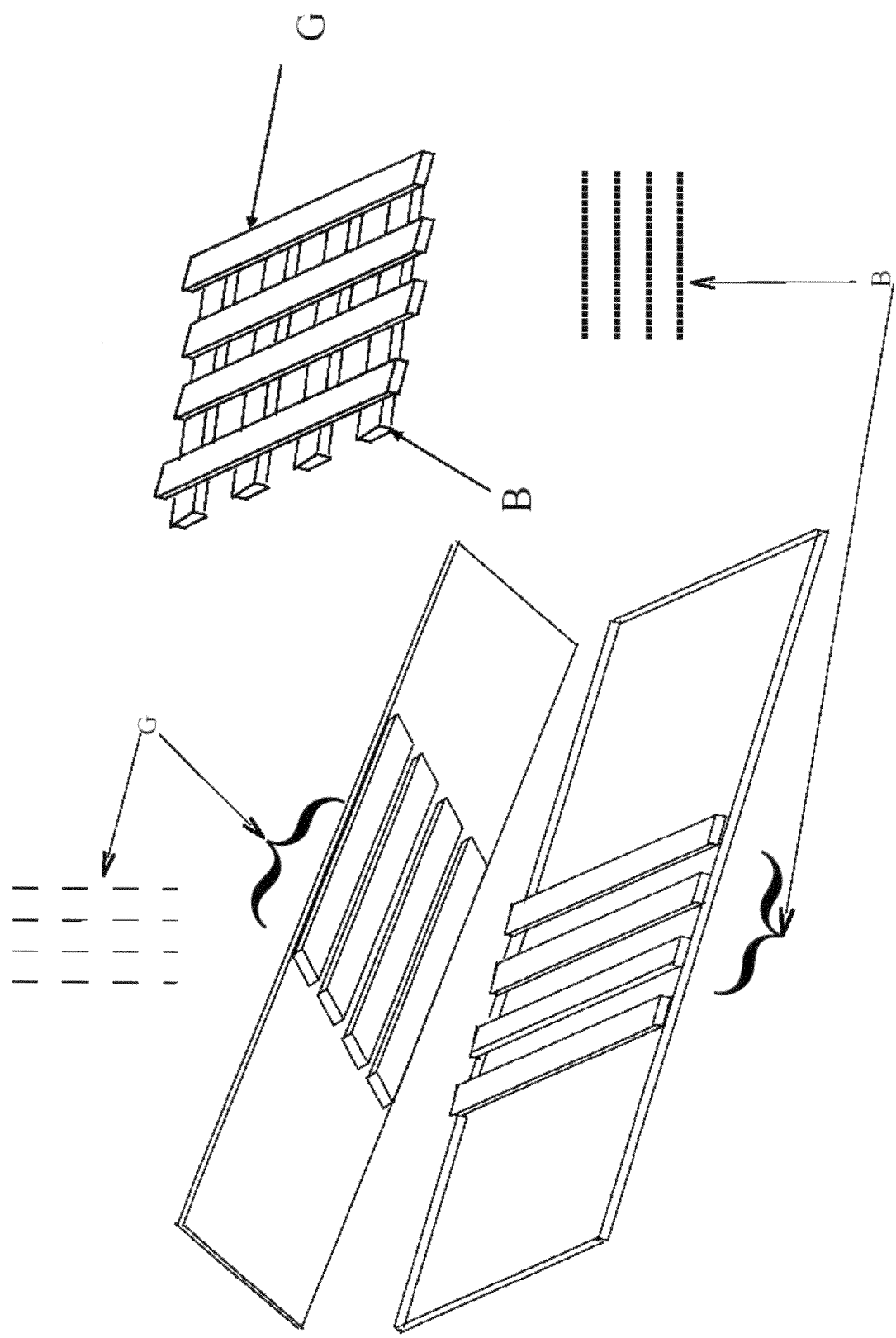

FIG. 4 shows a set of line electrode pairs. The pairs of line electrodes are obtained by placing two slides etched with electrodes opposite each other. One of the slides is functionalised, the other is not.

Figure 5:
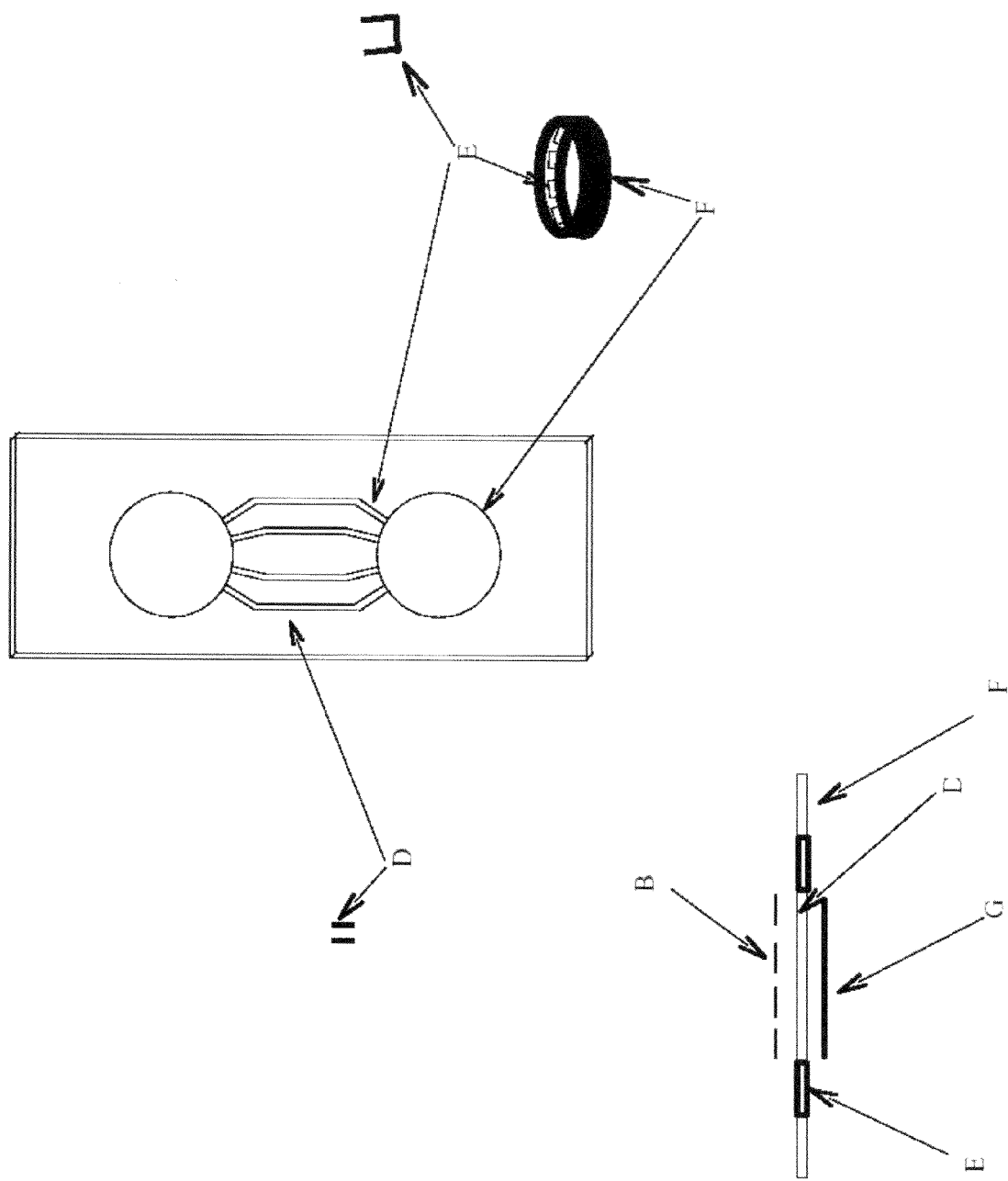

FIG. 5 shows a network of capillaries to intercalate between the sets of functionalised and non-functionalised electrodes.

Figure 6:
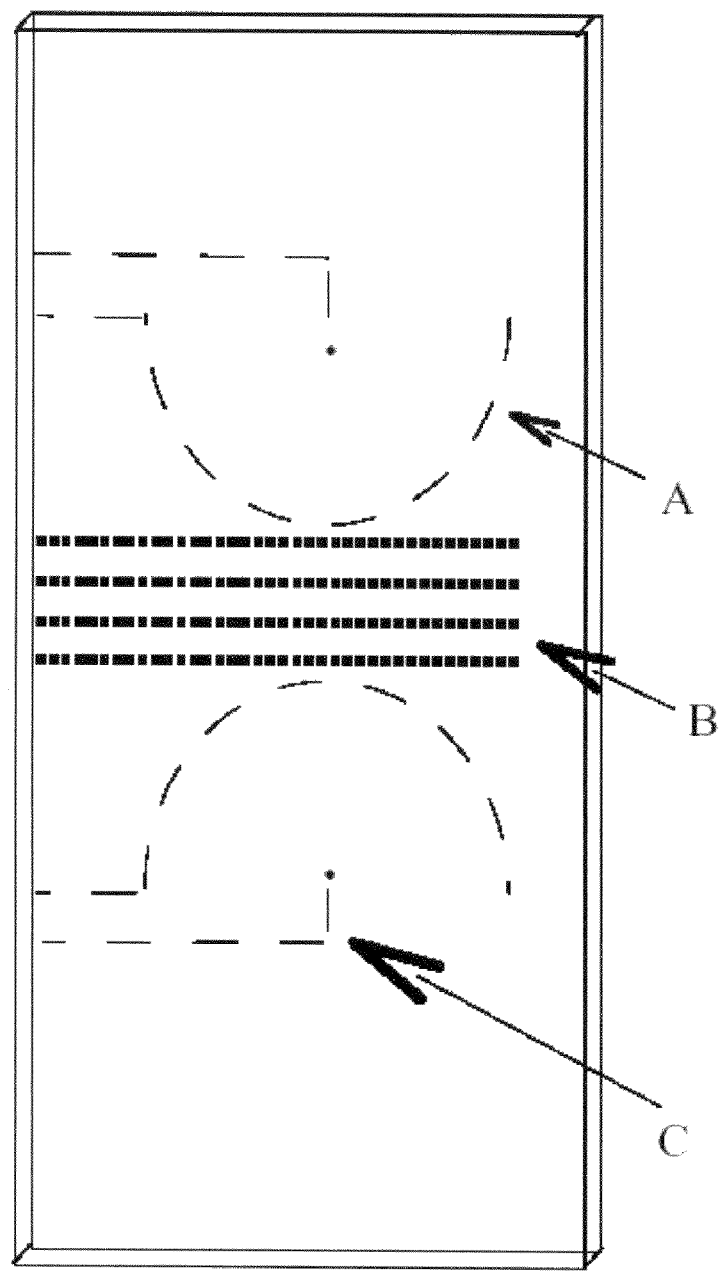

FIG. 6 shows a set of functionalised electrodes, completed by the curved binding electrodes and the reservoir electrodes.

Figure 7:
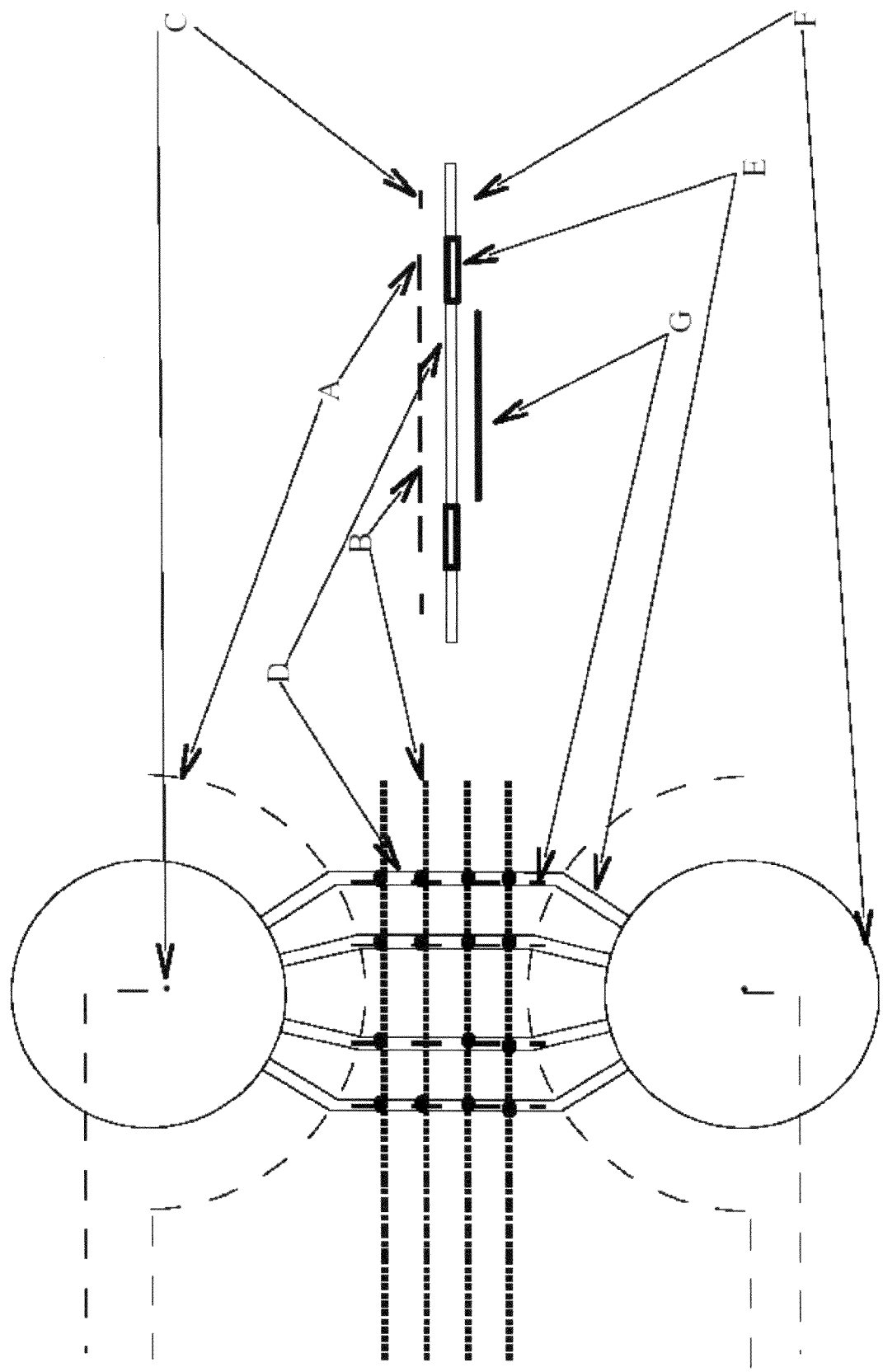

FIG. 7 shows a group of two sets of functionalised and non-functionalised electrodes around the capillary network.

Figure 8:
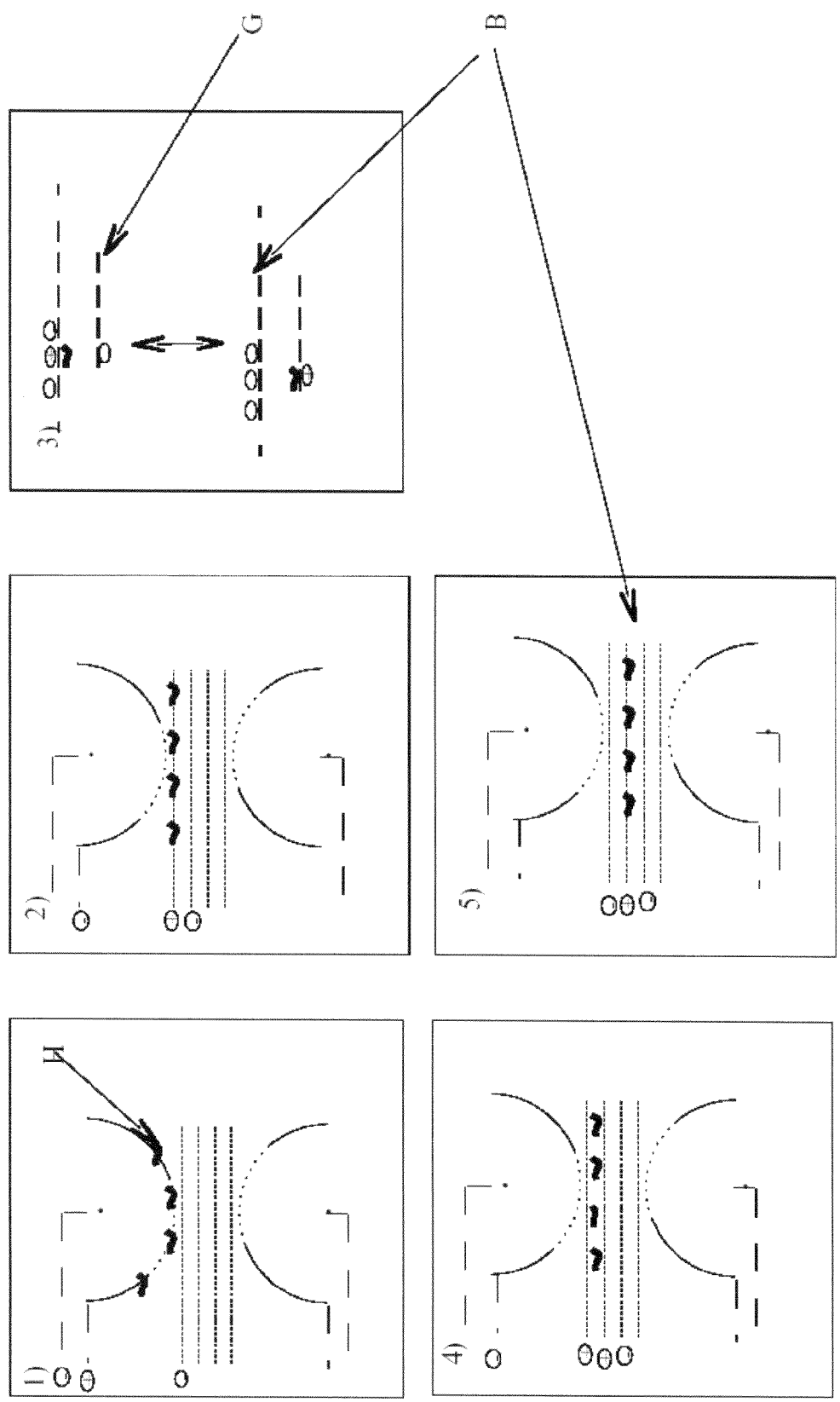

FIG. 8 shows a sequence of charges applied to the electrodes to make the targets migrate sequentially from one electrode to the other, so from one spot to the other.

Figure 9A:
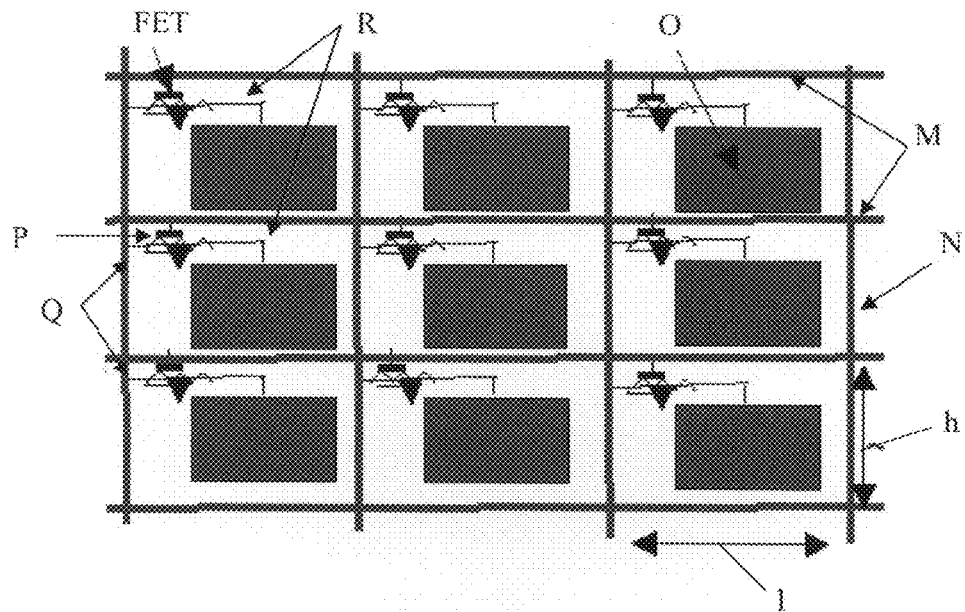

FIG. 9a shows a mesh replacing the set of functionalised electrodes for the impedance measurements with alternating current.

Figure 9B:
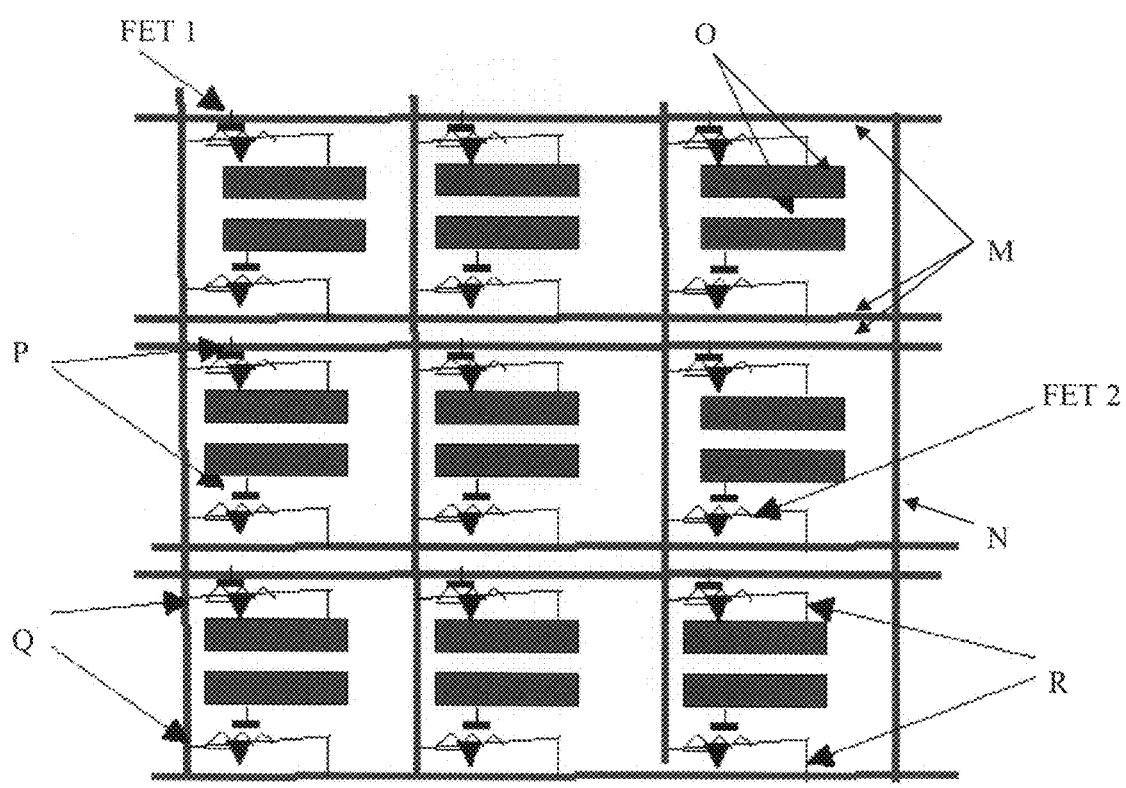

FIG. 9b shows another mesh replacing the set of functionalised electrodes for the impedance measurements with alternating current.

Figure 9C:
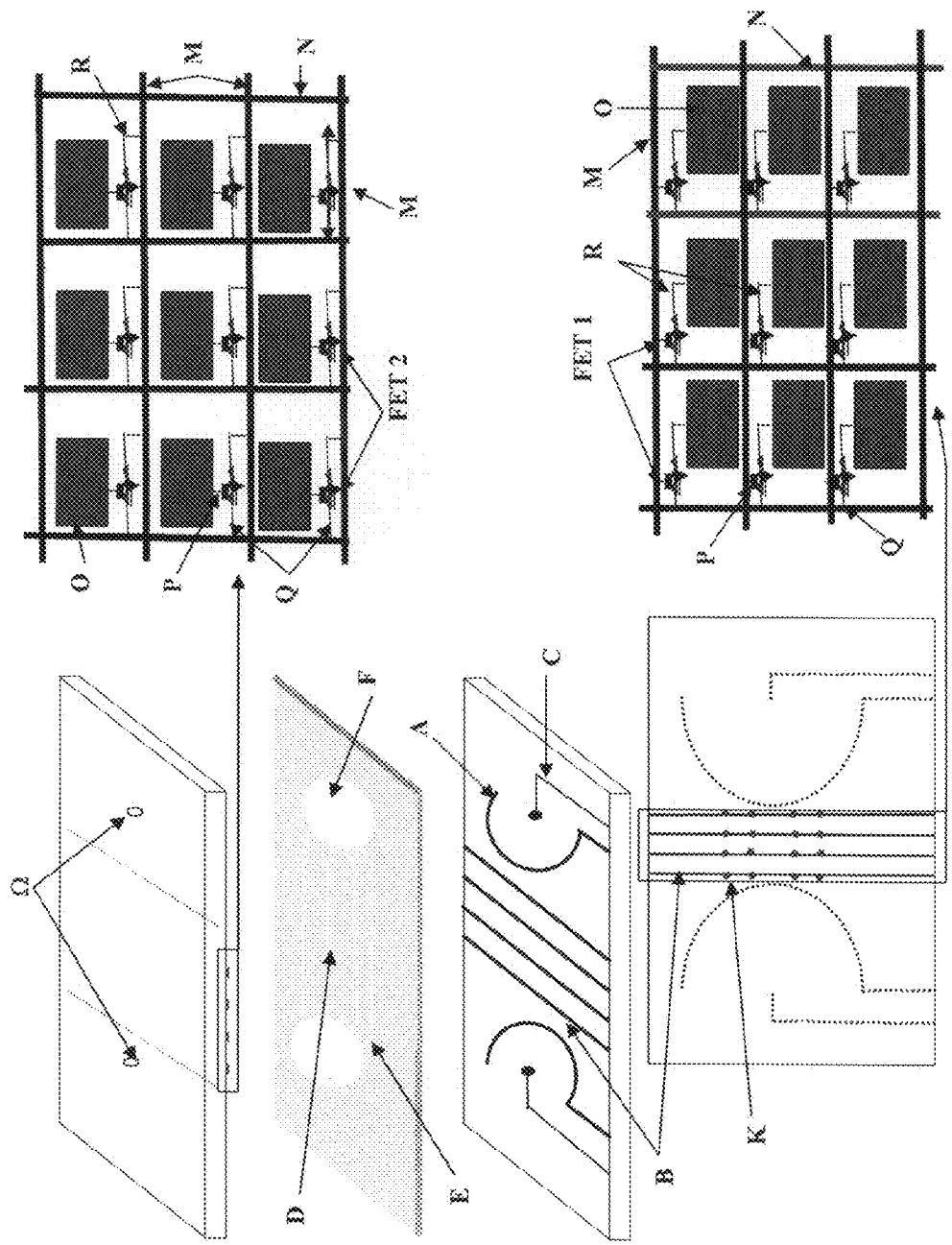

FIG. 9c shows the meshes intended to be placed respectively above and below a capillary network.

Figure 10:
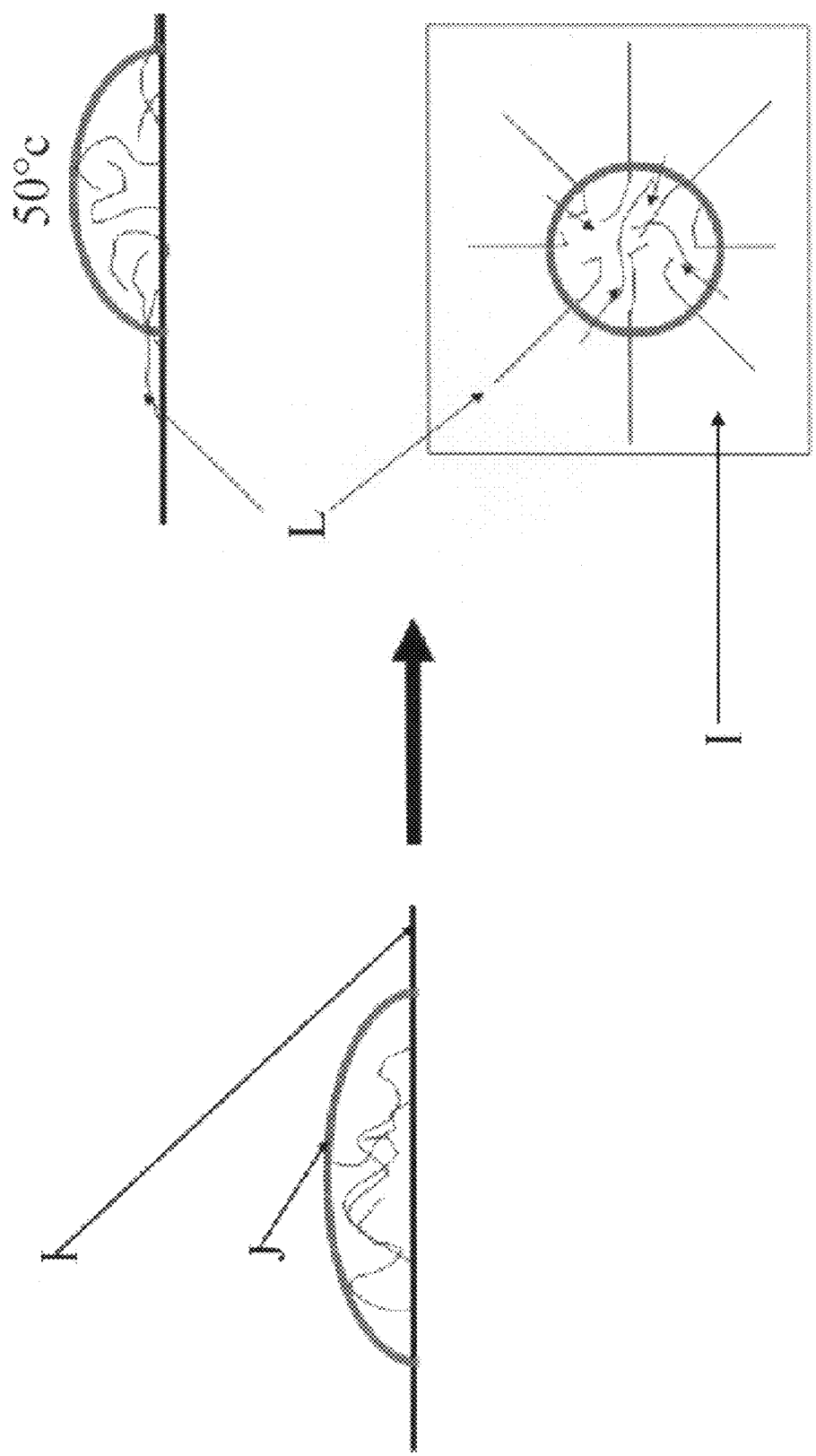

FIG. 10 shows DNA strands being attached to the wall by evaporation. On evaporating, the drop deposited will stretch out towards the centre of the spot.

Figure 11:
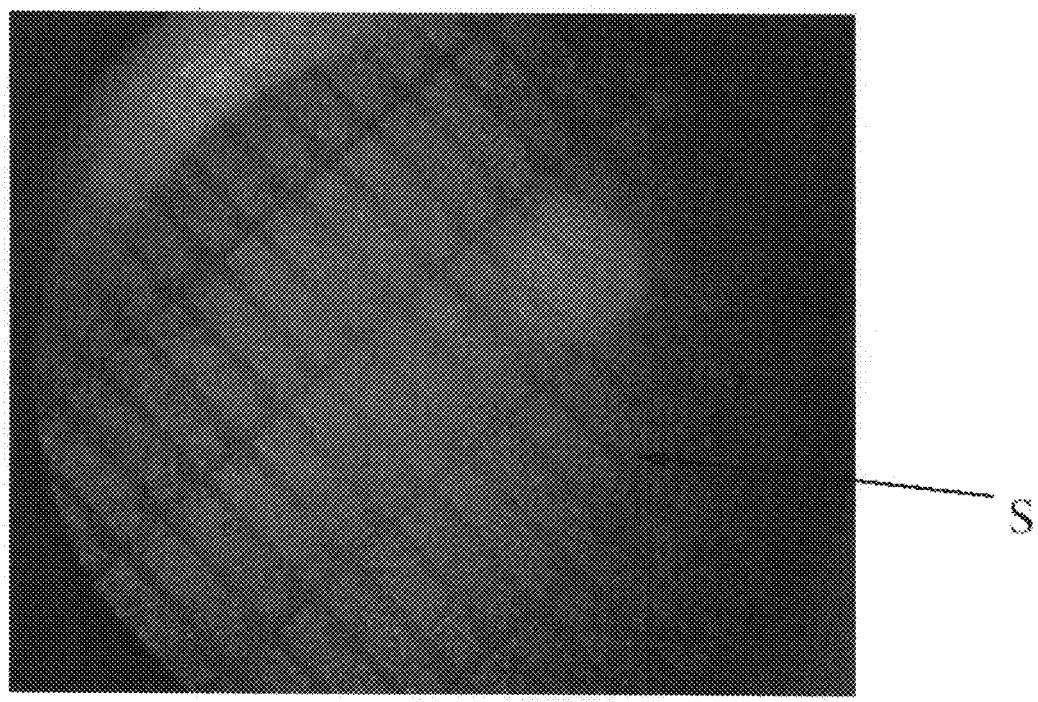

FIG. 11 shows an ITO electrode covered with elongated single stranded DNA probes.

Figure 12:
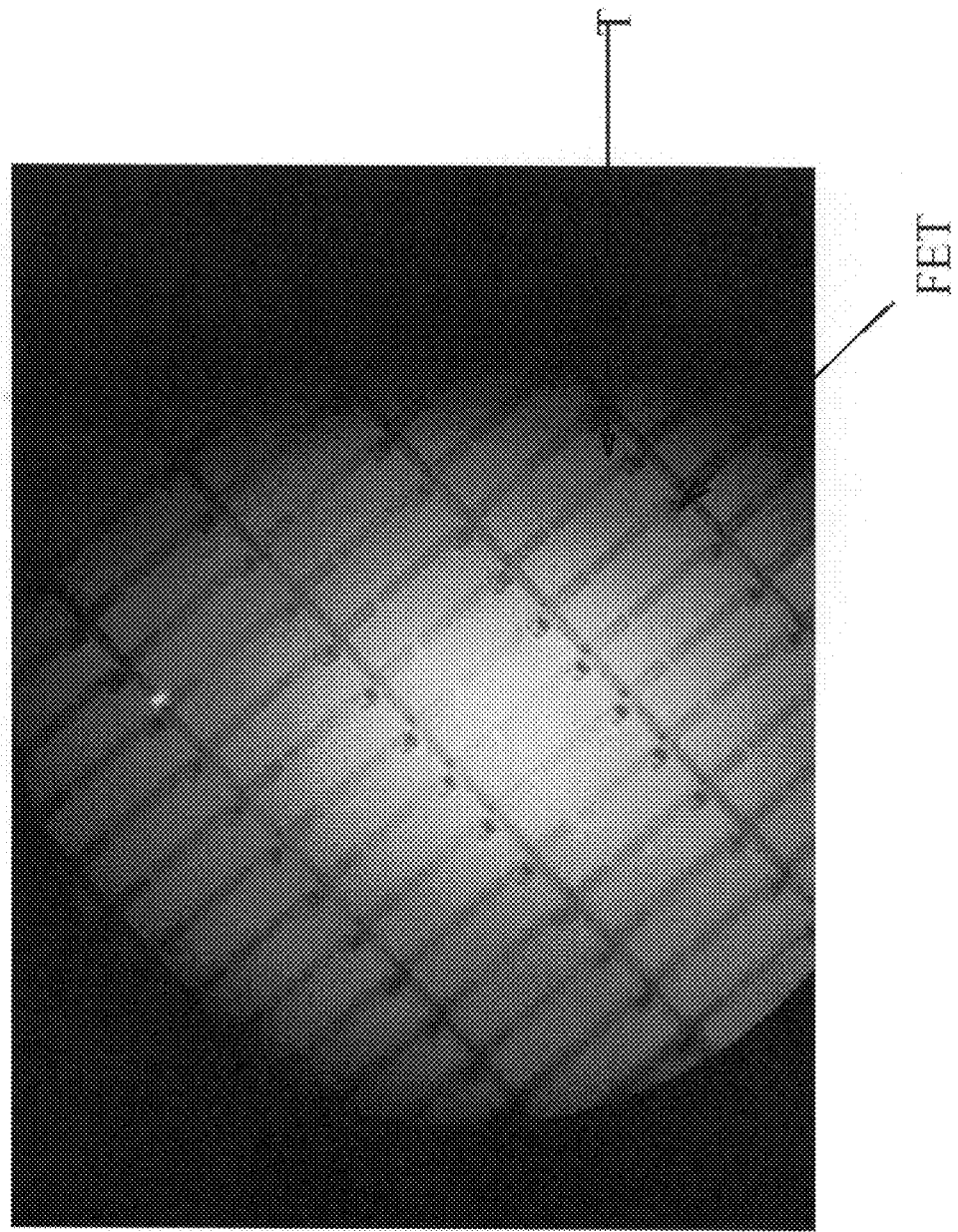

FIG. 12 shows an ITO electrode hybridised with a complementary DNA strand.

Figure 13:
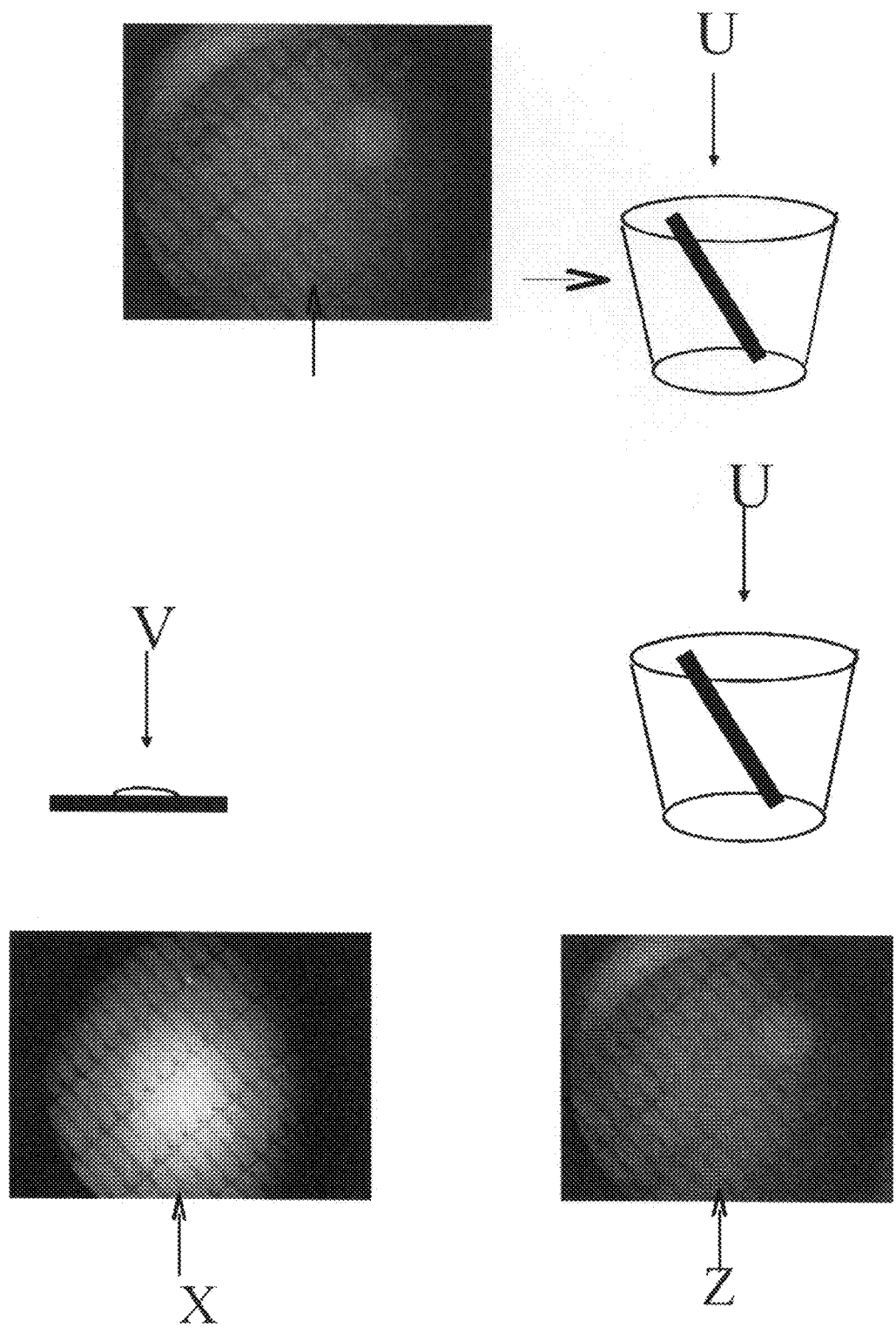

FIG. 13 shows different denaturing treatments. The fixing of the secondary probes onto the ITO electrodes resists the different most widely used denaturing treatments (0.1 M NaOH, 10% SDS, 95° C. . . . ), which makes it possible to regenerate the chip after use.

Figure 14:
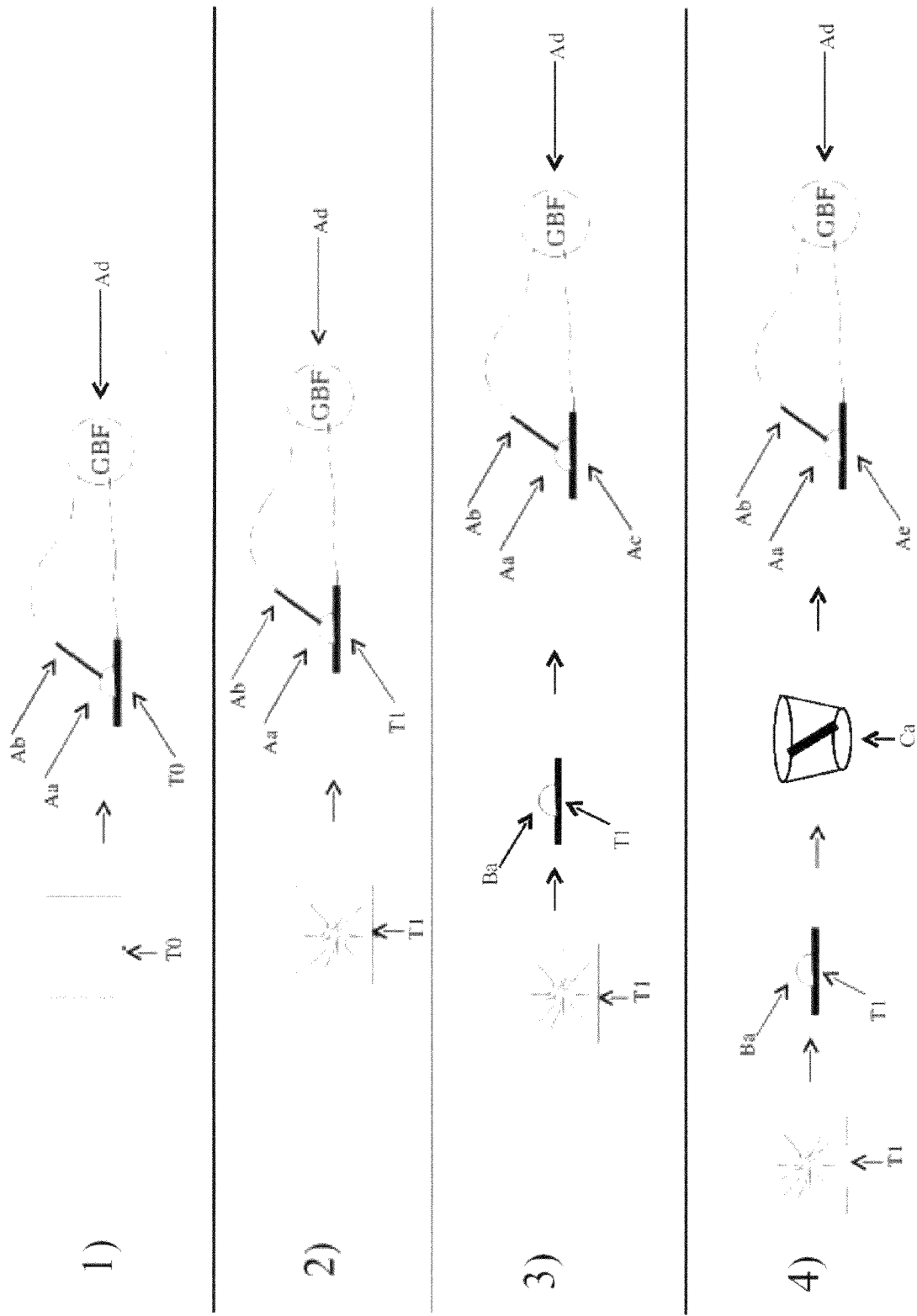

FIG. 14 shows measurements being taken. An impedance measurement is carried out, both on a naked spot electrode (FIG. 14.1) and also on an electrode functionalised with a 118-base single stranded DNA and obtained by combing a deposit of 0.1 μl of a 1 M DNA solution (FIG. 14.2). It appears that the impedance is higher for the electrode covered with single stranded DNA than for an electrode covered with a double stranded DNA duplex (FIG. 14.3 and 14.4).

Figure 15:
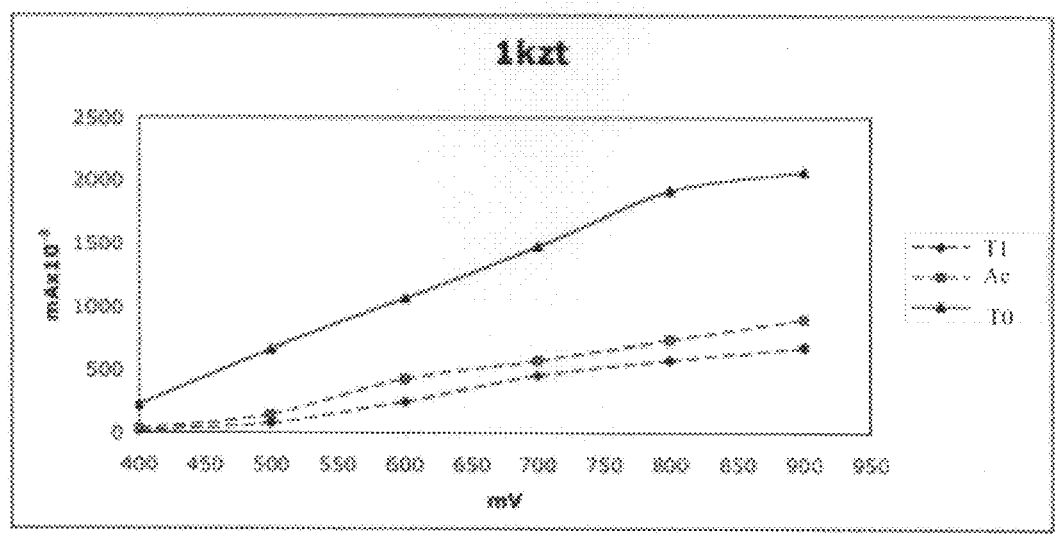

FIG. 15 shows the measurement of currents contingent on voltages applied to the spot electrodes.

Figure 16:
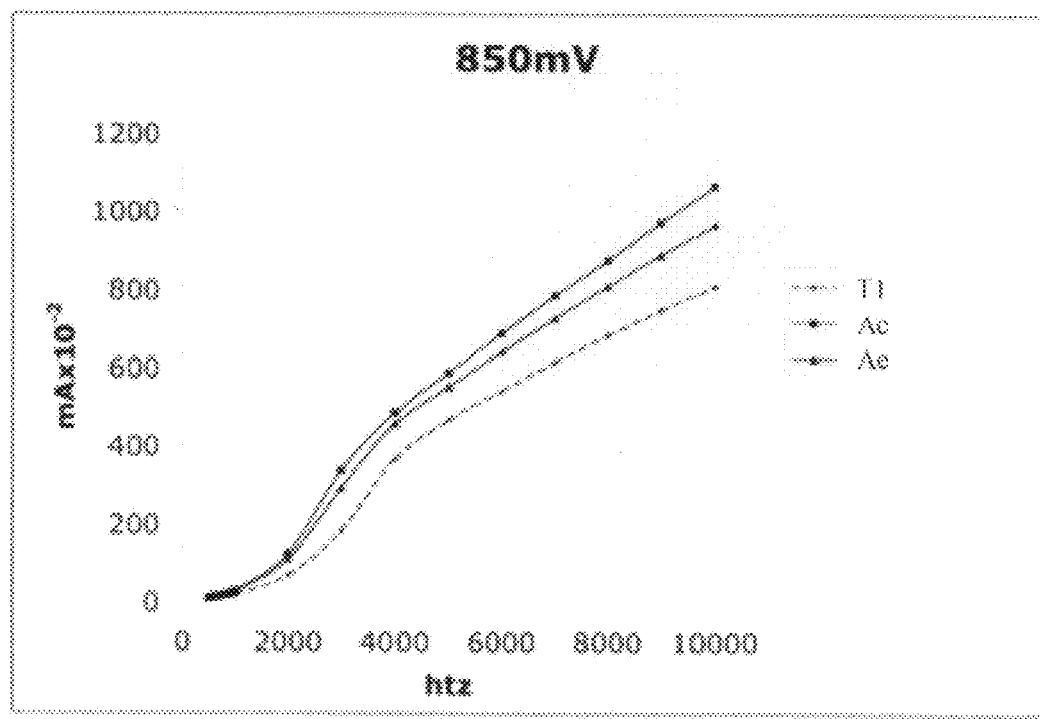

FIG. 16 shows the measurement of currents at a voltage of 850 mV contingent on the voltage frequency.

Figure 17A:
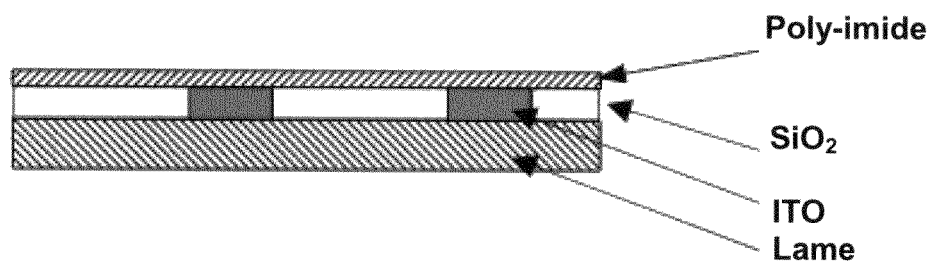

FIG. 17a is a diagrammatic cross-section of a molecular probe binding substrate.

Figure 17B:
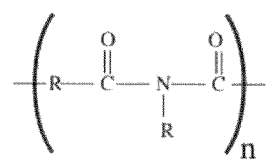
Figure 17C:
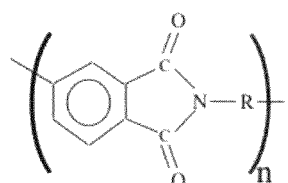
Figure 17D:
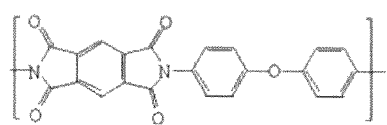

FIGS. 17b to 17d are formulae of polyimides.

Figure 18A:
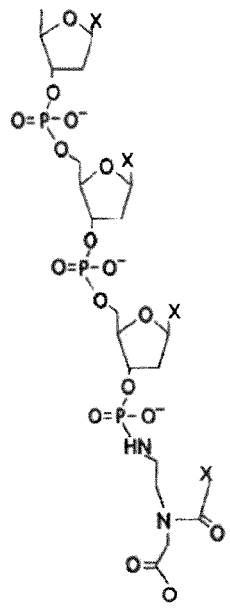
Figure 18B:
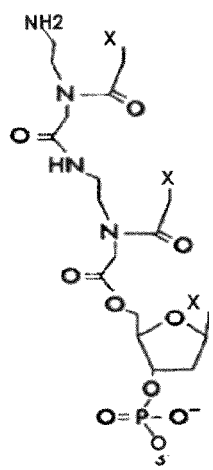
Figure 18C:
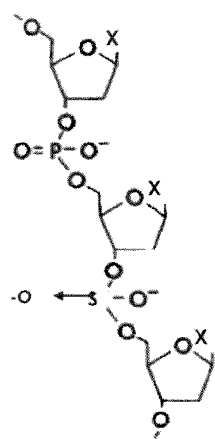

FIGS. 18a, 18b and 18c show mixed nucleic acid/Peptide Nucleic Acid compounds used as primary probes.

Figure 18D:
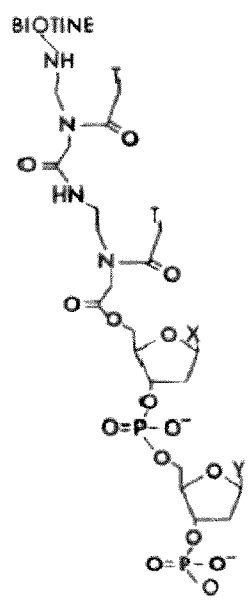
Figure 18E:
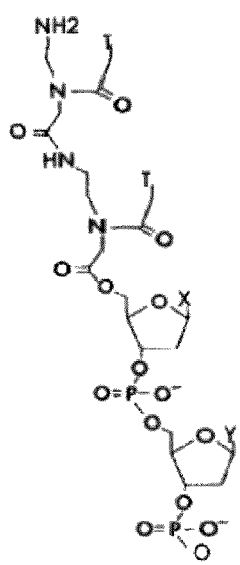
Figure 18F:
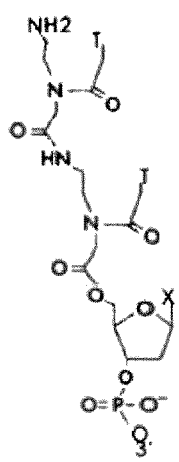

FIGS. 18d, 18e and 18f show primers of the (PNA)polyT-nucleic acid type.

Figure 19:
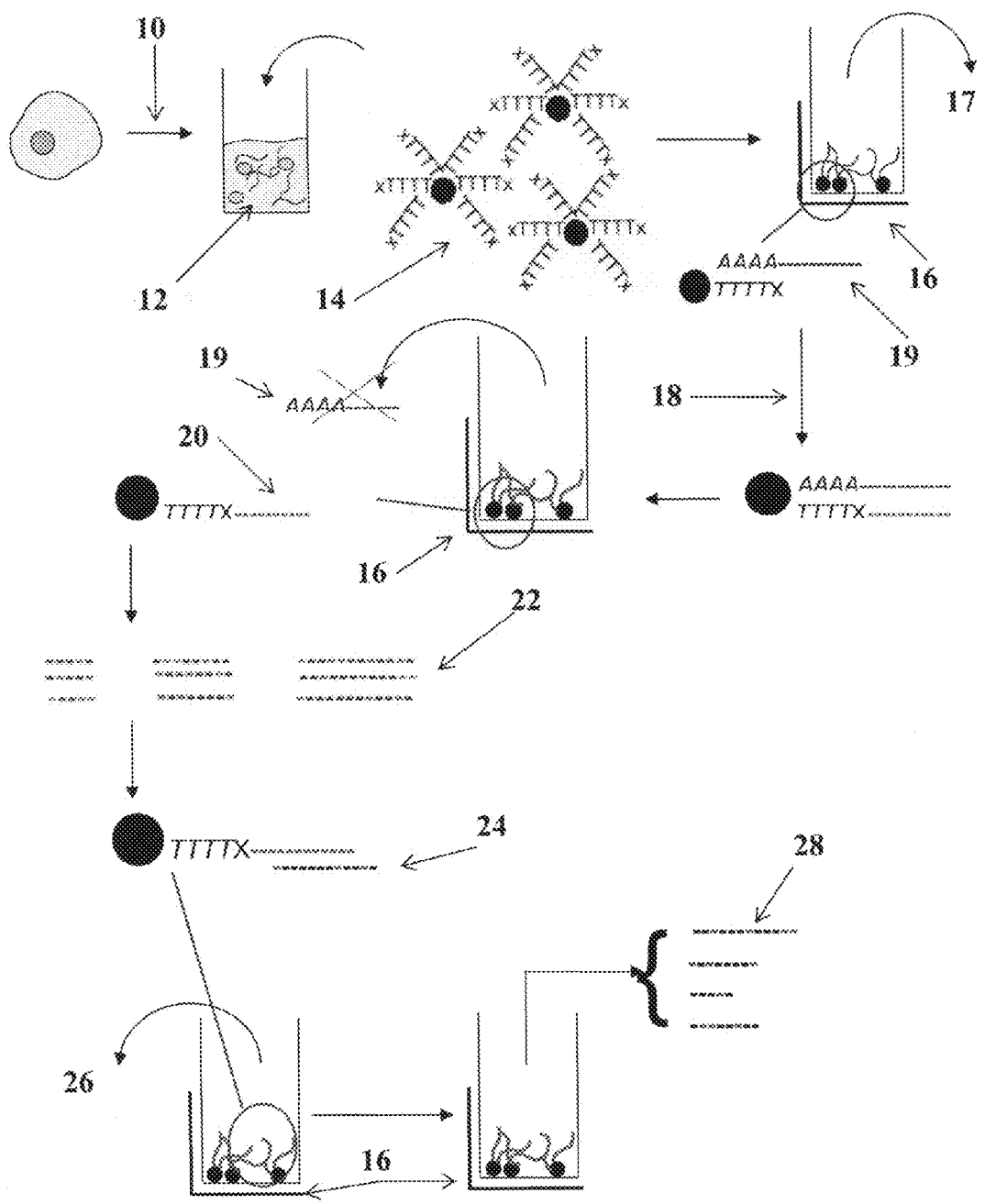

FIG. 19 gives an example of carrying out the method according to the invention.

Figure 20:
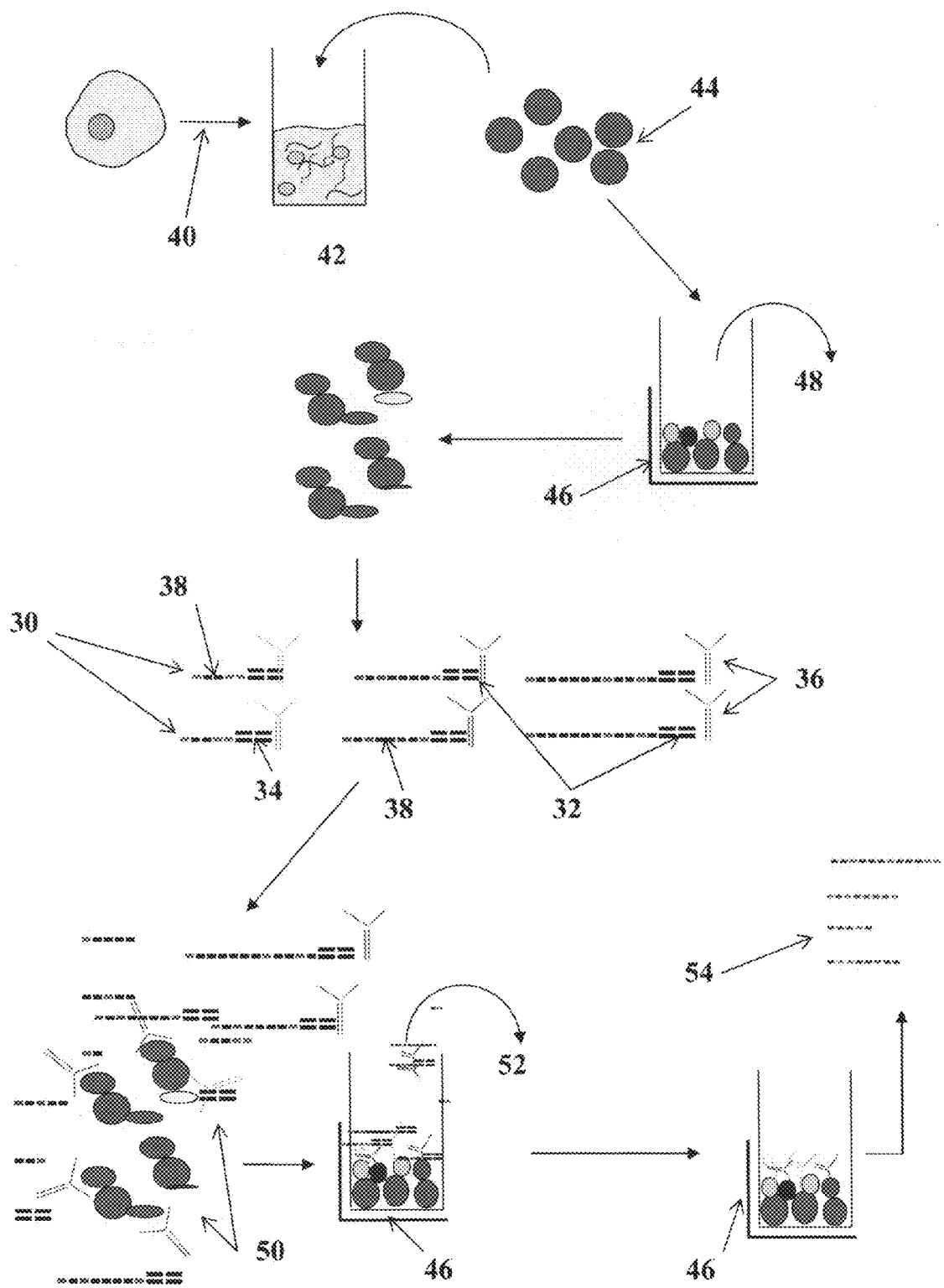

FIG. 20 gives another example of carrying out the method according to the invention.

Figure 21:
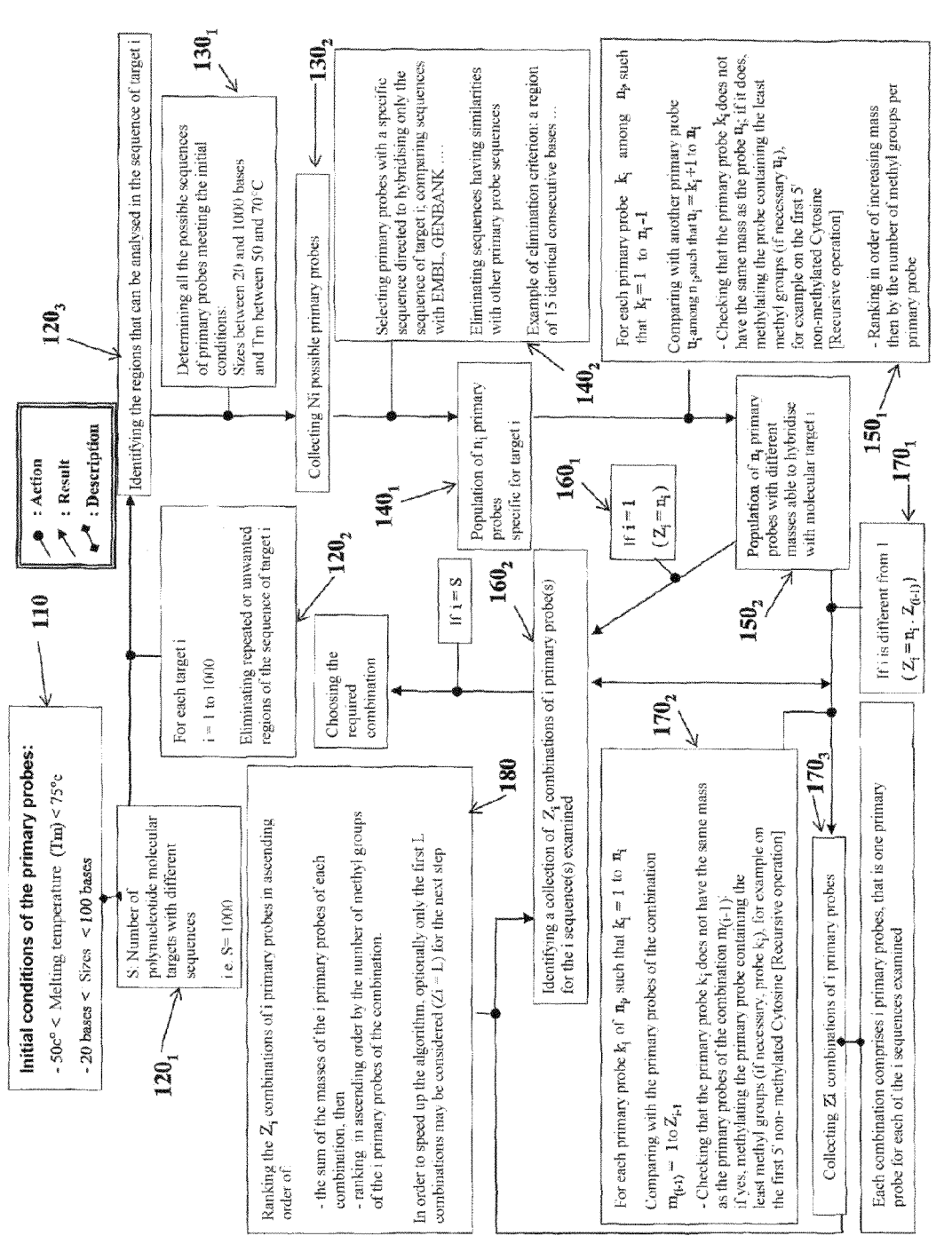

FIG. 21 shows the steps of an algorithm for preparing an array of primary probes.

EXAMPLES

The 2D electronic chip (2D Electro-Chip) makes it possible to identify and quantify, without previous labelling, the sequences of the bio-polymers constituting the eluted primary probes. The device is composed of a two-dimensional matrix of biological probes (array of secondary probes) organised in spots, associated with two sets of particular electrodes. The matrix is contained in a network of parallel capillaries interconnected by two reservoirs (one at each of their ends).

The capillary network and the electrode device make it possible to transport the targets (primary probes eluted according to the invention method) to each line of spots and to concentrate them there thanks to a succession of confining electric fields (controlled by the network of electrodes).

This device makes it possible to reduce the total reaction volume by preventing the passive diffusion of probes.

So this makes it possible to successively concentrate all the targets at each line of spots of the matrix. The limited quantity of material needed to carry out an experiment then depends only on the local concentration of targets at the line of spots and no longer on the total volume of the capillary network. This makes it possible to decrease the material to be used, proportionally to the ratio of the reaction volume of a traditional chip over the volume occupied by the probes confined to a line of the matrix (up to $10^8$ in theory).

The quantification of hybridised probes is done by measuring the impedance of the spot. Thence, it is no longer necessary to label the targets. The production technology coupled with the particular geometry chosen for the electrodes make it possible to increase the density of the spots up to a maximum of 800 to 20 000-30 000 spots on a surface of less than 18 $cm^2$. Moreover, the measurement artefacts due to the changes in conformation of the probes are minimised by the steric constraints imposed on the probes when they are grafted onto the surface of the electrodes. In order to carry out the constrained grafting, we have developed a grafting protocol on transparent metal alloys which do not require the functionalising of the probes.

Example 1

Binding the Nucleic Acids to the ITO Electrodes

The molecular probes much be attached sufficiently strongly to their substrate to resist the different denaturing treatments of the nucleic acids and to resist any electric fields used to manipulate the primary probes. In the context of measuring the rate of hybridisation of the nucleic acids by impedance, two main problems have been encountered, over and above the geometry of the electrodes: 1) Local structure defects in the materials can lead to sporadic resistances from one electron to another, causing artefacts in the impedance reading. 2) Functionalising the electrodes in order to graft the DNA molecules can disturb the measurement.

Added to these problems there are also the changes in impedance contingent on the conformation and size of the nucleic acid molecules.

The use of tin oxide or zinc oxide alloys such as: ITO, ATO, FTO, ZNO (optionally covered in polyimide for example Kapton®), minimises these problems.

This is because the methods for depositing these alloys are very standardised and reproducible, which makes it possible to obtain electrodes with very few defects. These materials are transparent and allow optical measurements.

Finally, the phosphate ion $PO_3^{2-}$ is adsorbed onto the surface of electrodes such as ITO (optionally covered with polyimide for example Kapton®), almost irreversibly. Since nucleic acids are naturally rich in phosphate, they are adsorbed onto an ITO deposit (optionally covered with polyimide for example Kapton®).

The proteins paired with phosphate functions can be bound to such supports in the same way or directly if they possess electrophilic groups. In order to do this, the proteins such as antibodies, can be paired with molecules such as phosphoric ethanolamine, which establishes a peptide function with the proteins (optionally in presence of glutaraldehyde) which is retained on the ITO alloys thanks to the phosphate function.

One of the possible protocols for fixing the secondary probes onto the ITO electrodes is as follows:

The ITO electrodes are:
1) Plunged for 20 minutes in a solution of ammonium and hydrogen peroxide.
2) Washed in distilled water.
3) Washed with propan-2-ol.
4) The probes are deposited in spots on the ITO electrodes, in a humid atmosphere.
5) The slide is then put into an oven at 50° C. to carry out the molecular combing of the DNA. As it evaporates, the deposited drop stretches the strands of DNA attached to the wall towards the centre of the spot as described in FIG. 10.

Since ITO is very electrophilic, it is necessary to insulate by an encapsulation process the portions of the electrodes which have not had probes grafted on, in order to avoid any non-specific capture of targets or primary probes. For example, a polypyrrole film can be used. The film is created by passing a current through the grafted electrodes in presence of a pyrrole solution. Pyrrole polymerises spontaneously with the action of the current and insulates the free portions of the electrodes. The electrodes can also be saturated by a small oligonucleotide which cannot hybridise in a stable manner with the targets, for example an ATA or TAT, etc. trimer. A network of electrodes functionalised by the single stranded DNA is obtained as shown in FIG. 11.

This network is capable of specifically hybridising the mRNA or cDNA primary probes as shown in FIG. 12.

The fixing of the secondary probes onto the ITO electrodes resists the different most widely used denaturing treatments (0.1 M NaOH, 10% SDS, 95° C. . . . ), which makes it possible to regenerate the chip after use (FIG. 13).

An alternative is to use secondary probes functionalised with pyrrole to carry out the grafting of the probes.

It is possible to use directly plates or microscope slides entirely covered with ITO and/or polyimide (Kapton®) in order to produce matrices of probes (nucleotide or protein) by direct deposition using the same method described for deposits on electrodes. The chips obtained are conventional networks used in the conventional way.

In certain conditions, it is advantageous to separate the ITO metallic electrodes deposited on a slide by $SiO_2$ (one molecular layer at least) in order to insulate the electrodes electrically, then to cover the electrodes with a layer of polyimide (one molecular layer at least about 10 to 40 nm thick) for grafting the molecular probes. The substrate obtained in this way shown in FIG. 17*a* is of the glass/$SiO_2$/polyimide and glass/ITO/polyimide type and makes it possible both to graft the molecular probes onto the substrate and measure the current and resistance of the capacitance type in order to detect the complexes formed on the support.

Examples of polyimide formulae are given in FIGS. 17*b*, 17*c* and 17*d*. FIG. 17*b* shows a linear polyimide and FIGS. 17*c* and 17*d* show aromatic heterocyclic polyimides, the formula in FIG. 17*d* is that of Kapton®.

Example 2

Measuring the Impedance

An impedance measurement is carried out, both on a naked spot electrode (FIG. 14.1) and also on an electrode functionalised with a 118-base single stranded DNA and obtained by combing a deposit of 0.1 µl of a 1 M DNA solution (FIG. 14.2).

It appears that the impedance is higher for the electrode covered with single stranded DNA than for an electrode covered with a double stranded DNA duplex (FIG. 14.3 and 14.4; FIG. 15). The presence of nucleic acids which have not hybridised only modifies very slightly the impedance measured at the spot electrode. The impedance is mainly due to molecules attached to the surface of an ITO electrode: the impedance is higher for the single strands than for the double strands (FIG. 16). So it is possible to carry out dynamic measurements to see the hybridisation kinetics.

The differences in impedance measured between the naked spot electrode, the spot electrode covered with single stranded DNA and the spot electrode covered with DNA/DNA duplex depend on the frequency of the fields (voltage) and the electric current applied, these differences making it possible to quantify the level of hybridisation (FIG. 16).

Example 3

Method of Separation and Analysis Applied to Proteins

The method can take different forms for use in measuring the concentrations of different proteins and their modifications in a mixture taken for example from a cell extract.

E. 1 The Method Necessitates

4) A set of magnetic particles (or a surface) that can strongly bind the proteins. Typically, mention can be made of polystyrene, nylon, nitrocellulose, etc. beads or membranes.

5) A stoichiometric mixture of antibodies, where each type of antibody is strongly (covalent) bound to a specific sequence of nucleic acid: the sequence tag. The sequence tag breaks down into one or two generic sequences that can be cut specifically and a sequence unique and specific for each type of antibody. The specific nucleotide sequence of the antibody gives an unequivocal signature to the antibody like a barcode.

6) An oligonucleotide chip, in which the probes of each spot comprise a complementary sequence to the specific portion of the sequence tag of one of the types of antibodies of the stoichiometric mixture of antibodies. Typically, this could be the impedance chips described above or any other chip such as the set of spots of the chip corresponding to the set of sequence tags used (one spot per sequence tag).

E.2 Operating Principle.

Starting from a cell extract, the proteins are attached to magnetic polystyrene particles. The polystyrene has the faculty of durably adsorbing proteins. An excess of beads is used compared with the concentration of proteins to avoid saturating the beads, thus limiting the steric hindrance. Depending on the desired study, proteins can be denatured or not. The beads and the bound proteins are then:

4) precipitated by a magnetic field,
5) isolated from the supernatant,
6) washed and recovered in a saline buffer.

The beads are then saturated with proteins that are inert for the system studied. For example, bovine serum albumin (for non-bovine studies), small size proteins exogenous to the species studied such as Kunixt inhibitor or else aliphatic chain amino acids such as leucine are used. Steps 1 to 3 are carried out again. Then the complete system of saturated beads-bound proteins is put with the equimolar mixture of tagged antibodies. The (monovalent) antibodies bind specifically to their target proteins immobilised on the beads. The quantity of each type of antibody bound is proportional to the quantity of each type of protein adsorbed onto the beads. In order to decrease the steric hindrance, the antibodies can be substituted by antibody fragments (or half-antibodies) obtained by papain digestion. Each half-antibody is "tagged" with a nucleic acid sequence. Steps 1 to 3 are carried out again. The antibodies (or half-antibodies) which have reacted are thus isolated and separated from those which have not reacted. The nucleic acid tag is cut off using the cutting sequence introduced. This can be a palindromic sequence, for example, or the target sequence of an abzyme . . . . In the case of a palindromic sequence, two particular solutions may be mentioned:

The palindromic sequence is introduced between the antibody and the specific sequence tag. In order to separate the sequence tag from the antibody, a sequence complementary to the cutting sequence and the relevant restriction enzyme, are simply added to the medium, which makes it possible to separate the antibody from the specific sequence tag.

Two cutting sequences are introduced respectively between the antibody and the specific sequence tag, and at the end of the sequence tag, such that these two sequences are complementary to each other. In hybridising, they form the specific cutting site for an enzyme which is subsequently introduced into the medium. The specific sequence tags are then released into the solution.

Once they are separated from the antibodies, the sequence tags supply a mixture of oligonucleotides in solution the quantities of which are proportional to those of the types of antibodies retained on the beads, and thus proportional to the different proteins and to their modifications present in the cell extract analysed. The mixture of nucleotides obtained can be analysed on a conventional DNA chip or a chip as previously described.

It is possible with this method to carry out a differential study of the proteins of two different cell extracts (without having to label the proteins directly). The antibody tags of the first extract are labelled with fluorescent labels of one colour (for example cy3) and the antibody tags of the second extract are labelled with fluorescent labels of another colour (for example cy5).

Each of these extracts is processed as described above, then the mixtures of representative tags recovered for each extract are put together volume for volume and hybridised on a chip. The reading of the chip for each colour gives the differential between the proteins of the two extracts.

E.3 Labelling the Antibodies

The antibodies are labelled with nucleic acid tags.

For example:

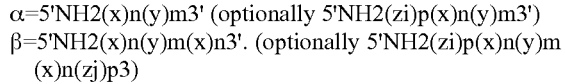

The amine function NH2 makes it possible to bind the nucleotide sequence to the antibody with a bridging agent such as glutaraldehyde and/or ethanolamine . . . . The nucleic acid polymer can optionally be bound directly to the antibody thanks to its amine function.

(x)n is a sequence of n nucleotides capable of forming a palindrome such that:

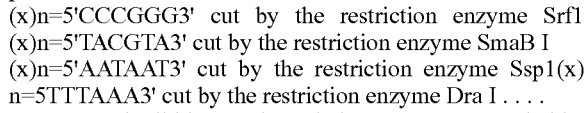

In general, all blunt end restriction enzymes are suitable. However the restriction sites with the lowest Tm are preferred.

Two solutions are possible:
α) Forming the cutting palindrome is carried out between a sequence intra tag and a free sequence (x)n (optionally (x)n(zj)n) added to the system at the same time as the restriction enzyme, to form the cutting palindrome,
β) The palindrome is intra molecular, the sequence (x)n is then introduced at the start and end of the tag.

The sequence y(m) is a nuclei acid sequence specific to a given type of antibody (comprising from 7 to 100 nucleotides). It acts like a molecular barcode and makes it possible to count the number and type of antibodies that have formed complexes.

The Z sequences minimise the unwanted pairings between intra or inter tag palindromic sequences. For example, the z sequences are defined such that:

The environment of palindromic sequences is made asymmetric by the zi and zj sequences, which thus increases the specificity of the cuts.

An alternative to the use of a restriction site to separate the tag from the antibody consists in using a complementary double stranded nucleic acid tag bound to the antibody by one of the two ends of one of the strands. Once the antibody/protein complexes are bound to the beads and isolated, the denaturing of the tags provides a mixture of free oligonucleotides in solution, the quantity of oligonucleotides being proportional to the antibodies retained on the beads. Then this mixture just has to be analysed on a chip, as described above.

Example 4

Mixed Method of Identifying and Quantifying Protein/mRNA

As described in E and A it is possible to successively isolate the proteins and mRNA of a cell and obtain two mixtures of nucleic acid polymers, primary probes and tag, representing respectively the mRNA and the proteins produced in a cell. These mixtures are hybridised on a chip (optionally two chips: one for the mRNA and another for the proteins) making it possible to evaluate in one analysis for the same batch of cells the mRNA and proteins.

A=curved binding electrodes (for example transparent ITO electrodes etched on a glass slide).

B=functionalised line electrodes (for example transparent ITO electrodes etched on a glass slide).

Bb=functionalised spot electrodes.
Bc=probe grafting guide or mask
Bd=filter polarising at 0°.
Be=filter polarising at α°.
Bf=transparent electrode substrate
Bg=grafted single stranded DNA probe.
Bh=light polarised in a single plane.
Bi=molecular DNA targets to be analysed.
Bj=double stranded DNA.

C=reservoir electrodes (for example transparent ITO electrodes etched on a glass slide).

D=capillary with no top or bottom (for example bored in Kapton®): mid plane.

E=capillary without lid with base (for example bored in Kapton® or PBMS): mid plane.

F=reservoir with no top or bottom (for example bored in Kapton®): mid plane.

G=non-functionalised line electrodes (for example transparent ITO electrodes etched on a glass slide).

I=ITO electrodes.
J=drop of DNA solution.
K=probe spots: unit of hybridisation.
L=elongated strand of DNA being absorbed onto the ITO electrode.
M=horizontal grid electrode
N=vertical source electrode.
O=spot electrode.
P=grid.
Q=source.
R=drain.

S=ITO electrode covered with elongated single stranded DNA probes (shown up with acridine orange, the red orange colour characteristic of a single strand).

T=functionalised spot electrode made of ITO with a 118-base oligonucleotide (S). The electrode is hybridised with a complementary strand of DNA (shown up with acridine orange, the green colour characteristic of a double stranded DNA/DNA duplex).

U=washing in a 0.1 M NaOH solution.
V=hybridising with the complementary strand.

X=spot electrode functionalised with a single strand washed with 1.0 M NaOH then hybridised with a complementary strand of DNA (shown up with acridine orange, the green colour characteristic of a double stranded DNA/DNA duplex).

Z=spot electrode after dehybridising in 1.0 M NaOH solution (shown up with acridine orange, the red orange colour characteristic of a single strand.

T0=naked ITO electrode.
T1=ITO electrode functionalised with a 118-base oligonucleotide.
Aa=electrophoresis buffer.
Ab=electrode at the surface of a drop of buffer.
Ad=low frequency generator.
Ac=spot electrode after hybridisation: covered with double stranded DNA.

Ba=Solution of DNA complementary to the sequences of the hybridised probes (secondary probes).
Ca=washing step.
Ae=spot electrode after hybridisation and washing.
FET=field effect transistor.
h=height of a square of mesh.
l=length of a square of mesh.
Q=Valves for injecting fluids in the chip reservoirs.

The invention claimed is:

1. A device for analyzing molecular targets contained in a complex mixture, said device comprising:
a capillary network allowing primary probes of different types to circulate, each type of primary probe being capable of being bound by a specific bond to one type of target among said molecular targets,
a matrix of secondary probes organized in spots inside said capillary network and capable of retaining a specific type of primary probe by specific bonding,
a network of functionalized electrodes, onto which the secondary probes are attached, this network being set out in such a way that each line of spots of the spot matrix is linked to one of the functionalized electrodes of said network, and
a network of non-functionalized electrodes, which is disposed in such a way that the capillary network is situated between the two networks of electrodes, wherein said network of functionalized electrodes is formed by a square mesh pattern of superimposed and coplanar line and column electrodes, and contains, in each square of the mesh, one spot electrode onto which the secondary probes are attached and which is connected to a line electrode and a column electrode of the mesh by a first field effect transistor, said first field effect transistor having a transistor drain connected to said spot electrode, a transistor grid connected to said line electrode and a transistor source connected to said column electrode, and wherein said networks of non-functionalized electrodes is formed by a square mesh pattern of superimposed and coplanar line and column electrodes, and contains, in each square of the mesh, one spot electrode connected to a line electrode and a column electrode of the mesh by a second field effect transistor, said second field effect transistor having a transistor grid connected to said spot electrode, a transistor drain connected to said line electrode and a transistor source connected to said column electrode, so that the field effect transistor acts as a detector, said second field effect transistor being configured so that a state of closure of said second field effect transistor is modified in function of electrical potential or current variation induced at its transistor grid when a voltage is applied to the spot electrode of the first field effect transistor.

2. The device according to claim 1, wherein it allows analysis of the molecular targets by using the analysis of the primary probes.

3. The device according to claim 2, wherein it makes it possible to measure the variations of impedance related to the hybridization of the primary and secondary probes.

4. The device according to claim 2, wherein it makes it possible to measure the hybridization of the primary and secondary probes by Surface Plasmon Resonance.

5. The device according to claim 2, wherein it makes it possible to measure the variation of polarized light caused by the formation of the primary probe-secondary probe hybrids.

6. The device according to claim 1, wherein the electrodes are etched in a thin layer on an insulating material.

7. The device according to claim 1, wherein the network of functionalized electrodes is situated above the capillary network and in that the network of non-functionalized electrodes is situated below the capillary network.

8. The device according to claim 1, wherein the network of functionalized electrodes is situated below the capillary network and in that the array of non-functionalized electrodes is situated above the capillary network.

9. The device according to claim 1, wherein each spot of functionalized electrodes is in each capillary of the capillary network.

10. The device according to claim 1, wherein it also comprises a reservoir at each end of the capillary network.

11. The device according to claim 10, wherein the reservoir contains an electrode, called the reservoir electrode.

12. The device according to claim 11, wherein the reservoir electrode contained in each reservoir is situated in the same plane as the network of functionalized electrodes.

13. The device according to claim 11, wherein it also comprises a first and a second supplementary link electrode situated respectively between the first reservoir electrode and a first functionalized electrode, and between the second reservoir electrode and a last functionalized electrode, such that the shortest distance between each link electrode and the corresponding reservoir electrode are identical at all points of the electrodes.

14. The device according to claim 10, wherein one of the reservoirs is formed by at least one transversal canal, which is connected upstream of all the capillaries of the capillary network and downstream of a detector.

15. The device according to claim 10, wherein each reservoir is bored in the thickness of a plate of appropriate material.

16. The device according to claim 1, wherein the network of non-functionalized electrodes is formed by a mesh of the type lines, columns of electrodes.

17. The device according to claim 16, wherein one of the networks of electrodes is earthed.

18. A method for analyzing molecular targets contained in a complex mixture comprising:
   a) providing the device of claim 1;
   b) contacting the mixture of molecular targets to be analyzed with the capillary network and a plurality of primary probes of different types, wherein each type of primary probe is capable of being bound by a specific bond to one type of target among the molecular targets, under conditions allowing a specific bond between said molecular targets and said primary probes so as to form a primary probe-target complexes, wherein each primary probe comprises a polynucleotide and wherein the polynucleotide of each type of primary probe is different from all of the polynucleotides of the other types of primary probes,
   c) optionally eliminating primary probes, which are not specifically bound with a molecular target,
   d) separating the molecular targets from the primary probes bound by a specific bond in said primary probe target complex, so as to recover the plurality of primary probes representing a fingerprint of the molecular targets to be analyzed, and
   e) analyzing the primary probes separated in step d) to thereby analyze the molecular targets.

19. The method according to claim 18, wherein step b) is carried out in solution to form primary probe-target complexes in solution.

20. The method according to claim 18, wherein the molecular targets of the mixture are bound to particles before being put in contact with the array of primary probes.

21. The method according to claim 18, wherein the molecular targets of the mixture are nucleic acids.

22. The method according to claim 18, wherein the molecular targets of the mixture are polypeptides or are both nucleic acids and polypeptides.

23. The method according to claim 18, wherein the polynucleotide of each primary probe is specific to a single type of molecular target in the mixture.

24. The method according to claim 18, wherein the plurality of primary probes further comprise a polypeptide portion associated with the polynucleotide, wherein each type of primary probe is capable, via its polypeptide portion, of recognizing and binding specifically with a unique type of polypeptide molecular target, and the polynucleotide portion of each type of probe is a tag specific to a unique type of molecular target.

25. The method according to claim 18, wherein step b) is carried out by mixing an excess of primary probes with the molecular targets.

26. The method according to claim 18, wherein step c) is carried out after the step of separating the primary probes contained in the probe-target complex, and prior to step e) of analyzing the separated primary probes.

27. The method according to claim 18, wherein step d) comprises immobilizing the molecular targets on magnetic particles, and applying a magnetic field to separate the immobilized molecular targets from the probe-target complexes and recovering the primary probes from the complexes.

28. The method according to claim 18, wherein step d) comprises immobilizing the molecular targets on particles, and centrifuging to separate the immobilized molecular targets from the probe-target complexes and recover the primary probes.

29. The method according to claim 18, wherein the polynucleotides of the plurality of primary probes are all of homogenous size and each has a determined sequence for obtaining primary probes that are different from each other.

30. The method according to claim 29, wherein step e) comprises using the matrix of secondary polynucleotide probes wherein each type of secondary polynucleotide probe is specific to a unique type of primary probe.

31. The method according to claim 30, wherein step e) comprises:
   i) putting the primary probes separated at step d) into contact with the matrix of secondary probes of different types, each type of secondary probe capable of being bound by a specific bond by hybridization to at least a portion of the primary probes, and
   ii) identifying the molecular targets and/or recovering and/or analyzing the polynucleotide portion of the primary probes hybridized to the secondary probes.

32. The method according to claim 31, wherein step ii) comprises circulating the primary probes over the matrix of secondary probes, which are immobilized in spots, by simple diffusion of the primary probes or by applying electrical potentials.

33. The method according to claim 32, wherein the electrical potentials are applied by at least one network of electrodes.

34. The method according to claim 31, wherein the specific bond between the secondary probes and the primary probes is a hybridization between complementary nucleotide sequences and in that the separation of hybrids formed between the primary probes and the secondary probes is obtained with controlled denaturing by raising the temperature.

35. The method according to claim 31, wherein at least one detector is used to measure variations of impedance related to the hybridization of the polynucleotide portions of the primary and secondary probes.

36. The method according to claim 31, wherein at least one detector is used to measure variations of polarized light caused by the hybridization of the polynucleotide portions of the primary and secondary probes.

37. The method according to claim 31, wherein at least one detector is used to measure hybridization of the polynucleotide portions of the primary and secondary probes by plasmonic surface resonance (PSR).

38. The method according to claim 18, wherein the polynucleotides of the plurality of primary probes are Peptide Nucleic Acids (PNAs).

39. The method according to claim 18, wherein the molecular targets are nucleic sequences representative of a transcriptome.

40. The method according to claim 18, wherein the molecular targets constitute a proteome.

41. The method according to claim 18, wherein step b) comprises putting a mixture, which may contain protein targets, into contact with the plurality of primary probes, wherein the primary probes further comprise antibodies or fragments of antibodies containing an antigen binding site, with each antibody or fragment of antibody being bound to a specific polynucleotide tag sequence, wherein each type of antibody or fragment of antibody recognizes a single type of protein to be analyzed, with conditions allowing a specific bond between said proteins and said antibodies or fragments of antibodies.

42. The method according to claim 41, wherein step d) comprises separating the proteins and the antibodies or fragments of antibodies bound by a specific bond, then separating each antibody or fragment of antibody and its specific polynucleotide tag, so as to recover a plurality of polynucleotide tags representing a fingerprint of the proteins to be analyzed.

43. The method according to claim 42, wherein analysis step e) comprises contacting the polynucleotide tags separated in step d) with the matrix of secondary probes of different types, wherein each type of secondary probe is being capable of being bound by a specific bond to one type of polynucleotide tag.

44. The method according to claim 43, further comprising quantitative detection of the proteins from the detection, and/or the recovery and/or the analysis of the polynucleotide tags bound to the secondary probes.

45. The method according to claim 18, wherein the polynucleotides of the primary probes all have different masses and at least one mass spectrometer is used to analyze the polynucleotides.

46. The method according to claim 41, wherein the polynucleotides of the primary probes all have different sizes and that the polynucleotides are analyzed by electrophoresis, chromatography, or filtration.

47. A device for analysing molecular targets contained in a complex mixture, said device comprising:
a capillary network allowing primary probes of different types to circulate, each type of primary probe being capable of being bound by a specific bond to one type of target among said molecular targets,
a matrix of secondary probes organised in spots inside said capillary network and capable of retaining a specific type of primary probe by specific bonding,
a network of functionalized electrodes, onto which the secondary probes are attached, this network being set out in such a way that each line of spots of the spot matrix is linked to one of the functionalized electrodes of said network, and
a network of non-functionalized electrodes which is disposed in such a way that the capillary network is situated between the two networks of electrodes, wherein said networks of functionalized electrodes is formed by a square mesh pattern of superimposed and coplanar line and column electrodes, and contains, in each square of the mesh, a first and a second spot electrodes connected to a line electrode and a column electrode of the mesh by a first and a second field effect transistors, respectively, said first field effect transistor having a transistor drain connected to said first spot electrode onto which the secondary probes are attached, a transistor grid connected to said line electrode and a transistor source connected to said column, and said second field effect transistor having a transistor grid connected to said second spot electrode, a transistor drain connected to said line electrode and a transistor source connected to said column electrode, so that the field effect transistor acts as a detector, said second field effect transistor being configured so that a state of closure of said second field effect transistor is modified in function of electrical potential or current variation induced at its transistor grid when a voltage is applied to the spot electrode of the first field effect transistor, and wherein the first and second spot electrodes of a line of first and second spot electrodes are separated from the other lines of first and second spot electrodes by two line electrodes.

\* \* \* \* \*